(12) United States Patent
Santin

(10) Patent No.: US 7,659,062 B2
(45) Date of Patent: Feb. 9, 2010

(54) GENE EXPRESSION PROFILING OF UTERINE SEROUS PAPILLARY CARCINOMAS AND OVARIAN SEROUS PAPILLARY TUMORS

(75) Inventor: Alessandro D. Santin, Little Rock, AR (US)

(73) Assignee: The Board of Trustee of the University of Arkansas System, Little Rock, AR (US)

( * ) Notice: Subject to any disclaimer, the term of this patent is extended or adjusted under 35 U.S.C. 154(b) by 190 days.

(21) Appl. No.: 10/859,020

(22) Filed: Jun. 1, 2004

(65) Prior Publication Data

US 2005/0037389 A1    Feb. 17, 2005

Related U.S. Application Data

(60) Provisional application No. 60/475,446, filed on Jun. 3, 2003.

(51) Int. Cl.
*C07H 21/04* (2006.01)
*C12Q 1/68* (2006.01)

(52) U.S. Cl. .............. 435/6; 435/91.1; 435/91.2; 536/23.1; 536/24.3

(58) Field of Classification Search ............... None
See application file for complete search history.

(56) References Cited

OTHER PUBLICATIONS

Maia et al. "Uterine serous papillary carcinoma arising inside an endometrial polyp removed by hysteroscopy" Gynaecological Endoscopy, vol. 9, pp. 331-335, 2000.*

* cited by examiner

*Primary Examiner*—Jeanine A Goldberg
(74) *Attorney, Agent, or Firm*—Benjamin Aaron Adler

(57) ABSTRACT

Oligonucleotide microarrays were used to profile and compare gene expression patterns between uterine serous papillary carcinoma and ovarian serous papillary carcinoma or normal endometrial epithelial cells. mRNA fingerprints readily distinguish the more biologically aggressive and chemotherapy resistant USPC from OSPC or NEC. Plasminogen activator inhibitor is the most highly up-regulated gene in OSPC relative to USPC, whereas the c-erbB2 gene product (HER-2/neu) is strikingly overexpressed in USPC relative to OSPC and may therefore represent a novel diagnostic and therapeutic marker for this highly aggressive subset of endometrial tumors.

4 Claims, 8 Drawing Sheets

GENE EXPRESSION PROFILING OF UTERINE SEROUS PAPILLARY CARCINOMAS AND OVARIAN SEROUS PAPILLARY TUMORS

CROSS-REFERENCE TO RELATED APPLICATION

This non-provisional patent application claims benefit of provisional patent application U.S. Ser. No. 60/475,446, filed Jun. 3, 2003, now abandoned.

BACKGROUND OF THE INVENTION

1. Field of the Invention

The present invention relates generally to the field of cancer research. More specifically, the present invention relates to gene expression profiling of uterine serous papillary carcinomas and ovarian serous papillary tumors.

2. Description of the Related Art

Ovarian serous papillary cancer (OSPC) represents the most common histological type of ovarian carcinoma and is the fourth leading cause of cancer-related death in women in the United States. Endometrial cancer is the most frequent cancer of the female genital tract with endometrioid (type 1) and serous papillary (type 2) being the most common cell types. Histologically indistinguishable to high grade serous ovarian carcinoma, uterine serous papillary cancer (USPC) has a propensity for early intra-abdominal, lymphatic and distant metastatic spread even at presentation and is characterized by a highly aggressive biological behavior. Unlike ovarian serous papillary cancer which is responsive to first line combined cisplatinum-based chemotherapy in 70% to 80% of the cases, uterine serous papillary cancer is a chemotherapy-resistant disease from outset, with responses to cytostatic agents in the order of 20% and of short duration.

Gene expression fingerprints representing large numbers of genes have the potential to allow precise and accurate grouping of tumors endowed with similar phenotype. Gene microarrays may identify cancers endowed with a more aggressive biologic behavior (i.e., rapidly metastatic tumors) that are unresponsive to standard adjuvant therapies and may thus allow improved prediction of response and clinical outcome. Consistent with this view, in large B-cell lymphomas and breast carcinomas, gene expression profiles have been shown to identify patients who are unlikely to be cured by conventional therapy.

In ovarian carcinoma, cDNA microarray technology has recently been used to identify numerous genes differentially expressed in normal and tumor derived ovarian epithelial cells. Interestingly, several of the most up-regulated genes encode surface or secreted proteins, such as Kop, SLPI and claudin-3, making these products attractive candidate biomarkers. In contrast, very little is known about the possible genetic diversity between ovarian serous papillary cancer and uterine serous papillary cancer, two histologically similar serous carcinomas characterized by a dramatically different biological behavior and response to chemotherapy. Thus, the prior art is deficient in understanding the molecular basis of the differences between ovarian serous papillary cancer and uterine serous papillary cancer. The present invention fulfills this need in the art by providing gene expression profiling for these two types of cancer.

SUMMARY OF THE INVENTION

High grade ovarian serous papillary cancer (OSPC) and uterine serous papillary carcinoma (USPC) represent two malignancies that are histologically indistinguishable but are characterized by markedly different biological behavior and response to chemotherapy. Understanding the molecular basis of these differences may significantly refine differential diagnosis and management, and may lead to development of novel, more specific and more effective treatment modalities for ovarian serous papillary cancer and uterine serous papillary carcinoma.

In the present invention, an oligonucleotide microarray with probe sets complementary to >10,000 human genes was used to determine whether patterns of gene expression may differentiate ovarian serous papillary carcinoma from uterine serous papillary carcinoma.

Unsupervised analysis of gene expression in ovarian serous papillary cancer and uterine serous papillary carcinoma identified 116 genes that exhibited >2-fold differences ($p<0.05$) and that readily distinguished ovarian serous papillary cancer from uterine serous papillary carcinoma. Plasminogen activator inhibitor (PAI-2) was the most highly overexpressed gene in ovarian serous papillary carcinoma when compared to uterine serous papillary carcinoma, while c-erbB2 was the most strikingly overexpressed gene in uterine serous papillary carcinoma when compared to ovarian serous papillary carcinoma. Over-expression of the c-erbB2 gene and its expression product (i.e., HER-2/neu receptor) was validated by quantitative real-time PCR as well as by flow cytometry on primary uterine serous papillary carcinoma and ovarian serous papillary carcinoma, respectively. Immunohistochemical staining of serous tumor samples from which primary ovarian serous papillary cancer and uterine serous papillary carcinoma cultures were derived further confirmed HER-2/neu as a novel molecular diagnostic and therapeutic marker for uterine serous papillary carcinoma.

In conclusion, gene expression fingerprints have the potential to predict the anatomical site of tumor origin and readily identify the biologically more aggressive uterine serous papillary carcinoma from ovarian serous papillary cancer. A therapeutic strategy targeting HER-2/neu may be beneficial in patients harboring chemotherapy-resistant uterine serous papillary carcinoma.

Moreover, unsupervised analysis of mRNA fingerprints readily distinguished uterine serous papillary carcinoma from normal endometrial epithelial cells and identified 139 and 390 genes that exhibited >5-fold up-regulation and down-regulation, respectively, in primary uterine serous papillary carcinoma compared to normal endometrial epithelial cells. Many of the genes up-regulated in uterine serous papillary carcinoma were found to represent oncogenes, adhesion molecules, and secreted proteins such as L1 cell adhesion molecule (L1CAM), claudin 3 and claudin-4, kallikrein 6 (protease M) and kallikrein 10, (NES1), interleukin-6, interleukin-18, urokinase plasminogen activator receptor (UPAR), and c-erbB2. Down-regulated genes in uterine serous papillary carcinoma included transforming growth factor beta receptor III, platelet-derived growth factor receptor alpha, SEMACAP3, ras homolog gene family, member I (ARHI), and differentially downregulated in ovarian carcinoma 1 (DOC1). High affinity epithelial receptor for *Clostridium perfringens* enterotoxin (CPE) claudin 4 was further validated through immunohistochemical analysis as a novel therapeutic marker for uterine serous papillary carcinoma. The results presented herein, which were obtained with highly purified primary tumor cultures, highlight novel molecular features of uterine serous papillary carcinoma and provide foundation for the development of new type-specific therapies against this highly aggressive variant of endometrial cancer.

DETAILED DESCRIPTION OF THE INVENTION

Figure 1:
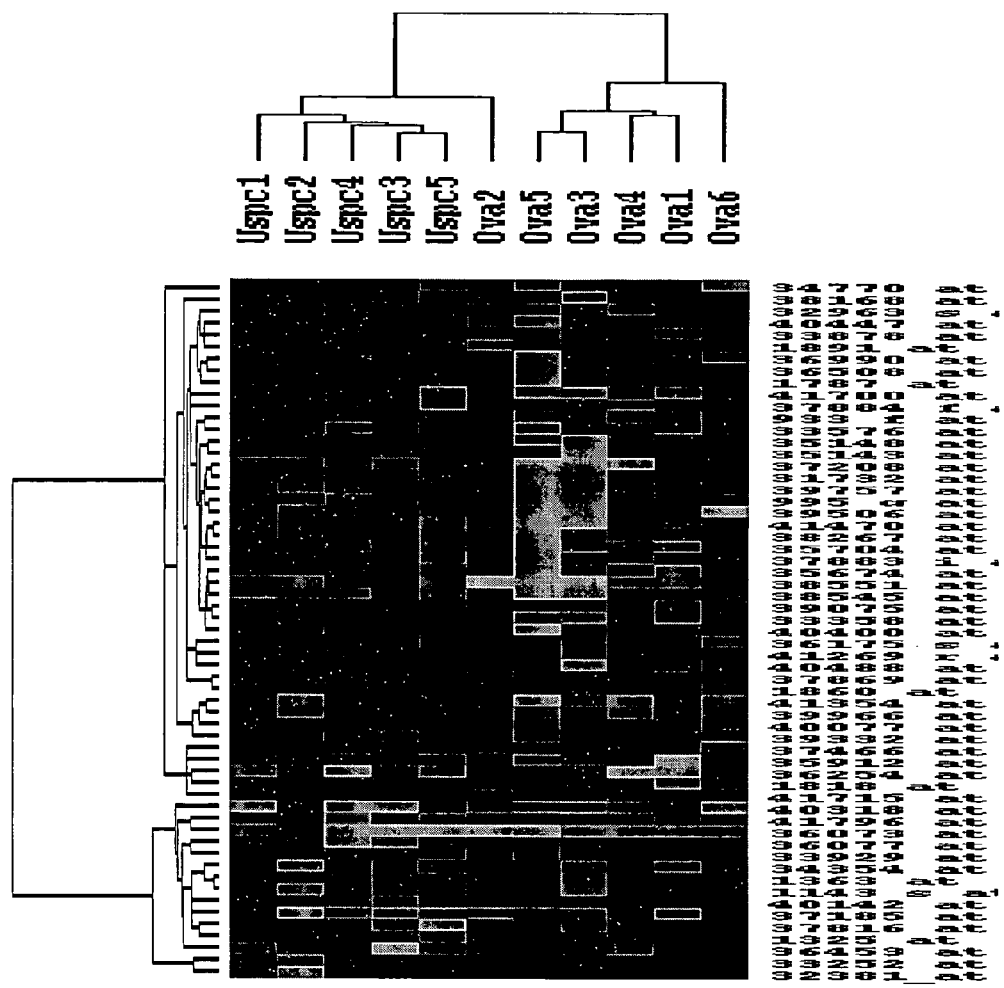
FIG. 1 shows hierarchical clustering of 59 genes with differential expression between 6 ovarian serous papillary cancer and 5 uterine serous papillary carcinoma groups (P<0.05) using a two-fold threshold. The cluster is color-coded using red for up-regulation, green for down-regulation, and black for median expression. Agglomerative clustering of genes was illustrated with dendrograms. The symbol for each gene is followed by the Affymetrix clone number of the corresponding oligonucleotide spotted on the array. Expression ratios comparing the two groups to each other are listed.

Advanced and/or metastatic serous papillary gynecologic tumors, regardless of their ovarian or uterine origin, are currently treated as a single disease. However, uterine serous papillary carcinoma is likely derived from metaplastic Mullerian epithelium, whereas ovarian serous papillary cancer is likely derived from the ovarian surface epithelium. Dramatic difference in response to standard cisplatinum-based chemotherapy is commonly reported for these histologically indistinguishable serous carcinomas. Hence, it is probable to have significant diversity in gene expression between these two types of tumors.

Ovarian Serous Papillary Carcinoma vs. Uterine Serous Papillary Carcinoma

All 5 uterine serous papillary cancer patients evaluated in this study either developed progressive disease during chemotherapy or recurred within six months from the end of treatment. In contrast, four out of five of the ovarian serous papillary cancer patients responded completely to standard adjuvant chemotherapy treatment. To study differential gene expression in highly enriched populations of epithelial tumor cells, short-term primary tumor cultures were used in the following study to minimize the risk of a selection bias inherent in any long term in vitro growth.

Hierarchical clustering of gene expression levels within the samples led to unambiguous separation of ovarian serous papillary carcinoma from uterine serous papillary carcinoma. Two hundred twenty seven genes were differentially expressed between ovarian serous papillary carcinoma and uterine serous papillary carcinoma, with 116 genes having at least two-fold differences between the two groups. Of interest, OSPC2, the only ovarian serous papillary cancer patient with mixed clear cell features included in the present analysis, clustered with uterine serous papillary carcinoma. These data are congruent with a recent report that clear cell ovarian tumors present a distinctive molecular signature from pure high grade ovarian serous papillary cancer. Thus, the following findings add to previous knowledge showing that clear cell tumors, a variant of ovarian cancer with a particularly unfavorable prognosis, express a molecular signature closer to that of the more aggressive uterine serous papillary carcinoma.

Lysophosphatidic Acid

Some of the differentially expressed genes may have diagnostic and therapeutic applications. For example, elevated serum levels of lysophosphatidic acid (LPA) are found in more than 90% of ovarian cancer patients and the level of lysophosphatidic acid in plasma has been proposed as a potential biomarker for this disease. In addition, lysophosphatidic acid signaling may have a role in the progression of ovarian cancer cells through stimulation of cellular proliferation, enhanced cellular survival and suppression of apoptosis. It seems therefore likely that the higher lysophosphatidic acid receptor expression found in ovarian serous papillary cancer relative to uterine serous papillary carcinoma may represent a distinctive marker that plays a role in transduction of growth-promoting signals from high local concentrations of lysophosphatidic acid. Consistent with this view, phospholipase C, another gene that is differentially overexpressed in ovarian serous papillary cancer relative to uterine serous papillary carcinoma, has been previously reported to contribute to lysophosphatidic acid production in ovarian cancer cells.

Plasminogen Activator Inhibitor-2

Plasminogen activator inhibitor-2 (PAI-2), a protein capable of inhibiting invasion, may represent a molecular biomarker for several human tumors including ovarian carcinomas. Over-expression of plasminogen activator inhibitor-2 in epithelial ovarian cancer has been previously identified as a favorable prognostic factor. Indeed, high plasminogen activator inhibitor-2 expression in invasive ovarian tumors seems to be limited to a group of ovarian serous papillary cancer patients which experience a more prolonged disease-free and overall survival. High expression of plasminogen activator inhibitor-2 in ovarian serous papillary cancer relative to uterine serous papillary carcinoma may indicate a biologically less aggressive disease.

Glypican-1 and Syndecan-2

Membrane-associated heparan sulfate proteoglycans are thought to play important roles in many aspects of cell behavior, including cell-cell and cell-extracellular matrix adhesion and growth factor signaling. Two families of polypeptides appear to carry the majority of heparan sulfate on mammalian cells: glypicans, which are attached to the plasma membrane via glycosylphosphatidylinositol (GPI) anchors, and syndecans, which are transmembrane proteins. Convincing evidence has recently been provided that glypican-1 can interact with FGF-2 and stimulate signaling of the FGF receptor. Importantly, whereas glypican-1 and FGF receptor 2 genes were expressed at higher levels in ovarian serous papillary cancer relative to uterine serous papillary carcinoma, syndecan-2 gene expression was significantly higher in uterine serous papillary carcinoma as compared to ovarian serous papillary cancer. These data therefore support a major difference in the expression of heparan sulfate proteoglycans between these two tumor types. Furthermore, because bFGF is produced by ovarian serous papillary cancer cells and can bind to FGF receptor 2 expressed on these tumors, the combined overexpression of glypicans and FGF receptor 2 genes found in ovarian serous papillary cancer cells may represent a common molecular abnormality with important functional consequences for the progression of ovarian serous papillary cancer.

Insulin Receptor

Over-expression of the insulin receptor by ovarian serous papillary cancer cells has been reported and is able to mediate a proliferative response in ovarian cancer cells. Results reported herein indicate that ovarian serous papillary cancer cells differentially overexpressed the insulin receptor gene relative to uterine serous papillary carcinoma. These results suggest a role for insulin receptor in the growth and regulation of ovarian serous papillary cancer cells, but not in uterine serous papillary carcinoma.

c-erbB2

Unlike ovarian serous papillary cancer, there have been few studies aimed at identifying molecular markers characteristic of uterine serous papillary carcinoma. Of particular interest, the c-erbB2 gene was the most highly overexpressed gene in uterine serous papillary carcinoma with over 17-fold up-regulation relative to ovarian serous papillary cancer cells. Furthermore, GRB7, a gene tightly linked to c-erbB2 and previously reported to be co-amplified and co-expressed with c-erbB2 in several cancer types was also highly differentially expressed in uterine serous papillary carcinoma compared to ovarian serous papillary cancer cells. The striking overexpression of the c-erbB2 gene product (HER-2/neu) on uterine serous papillary carcinoma may therefore represent a distinctive molecular marker for these tumors and may also provide insights into the disproportionately poor prognosis of uterine serous papillary carcinoma relative to ovarian serous papillary cancer. Consistent with this view, previous studies have reported that amplification of this gene in a subset of ovarian cancer patients is associated with resistance to chemotherapeutic drugs and shorter survival. High overexpression of the c-erbB2 gene strongly suggests that Herceptin™ monoclonal antibody, a humanized anti-HER-2/neu antibody that has shown great promise for treatment of metastatic breast cancers overexpressing HER-2/neu protein, may be a novel and potentially highly effective treatment option for uterine serous papillary carcinoma.

Collectively, the data presented herein show that ovarian serous papillary cancer and uterine serous papillary carcinoma, two diseases where further molecular characterization is needed to improve differential diagnosis and therapeutic strategies, can be readily discriminated by gene expression profiles. These findings suggest that global gene expression signatures can be an important adjunct to the morphology-based classification schemes for serous papillary tumors currently used.

Uterine Serous Papillary Carcinoma vs. Normal Endometrial Epithelium

Hierarchical clustering of gene expression levels led to unambiguous separation of uterine serous papillary carcinoma from normal endometrial epithelial cells (NEC), with 529 genes having at least five-fold differences between the two groups. The known function of some of these genes may provide insights to the molecular pathogenesis and the highly aggressive biologic behavior of uterine serous tumors while others may prove to be useful diagnostic and therapeutic markers against this disease.

Cyclin-Dependent Kinase Inhibitor 2A

The cyclin-dependent kinase inhibitor 2A (CDKN2A) gene was found to be the most highly differentially expressed gene in uterine serous papillary carcinoma with over 101-fold up-regulation relative to normal endometrial epithelial cells. Importantly, CDKN2A gene is a putative oncosuppressor gene encoding two unrelated cellular growth inhibitors in different reading frames. One is p16, which regulates retinoblastoma protein (pRb)-dependent G1 arrest, and the second is p14ARF, which blocks MDM2-induced p53 degradation resulting in an increase in p53 levels that leads to cell cycle arrest. Although loss of p53 function is considered critical for the molecular pathogenesis of uterine serous papillary carcinoma, it is only recently that abnormality of the Rb pathway was suggested to define a subgroup of aggressive endometrial carcinomas with poor prognosis. Quantitative real-time PCR results investigating the expression of both p16 and p14ARF in the uterine serous papillary carcinoma series described below showed extremely high levels of both transcripts, suggesting that the marked overexpression of the CDKN2A gene may be attributable to a negative feedback loop due to the loss of function of both pRb and p53 proteins. Consistent with this view, an inverse relationship between expression of p16 and p14ARF proteins and the presence of normal or functional Rb and p53 in human cancer cells has been previously demonstrated. Thus, the data presented below suggest for the first time that CDKN2A gene overexpression may represent a consistent genetic anomaly of uterine serous papillary carcinoma secondary to an auto-regulatory feedback loop due to a disruption of both the p16-CDK4/cyclin D1-pRb pathway (RB pathway) and the p14ARF-MDM2-p53 pathway (p53 pathway).

Lipocalin-2

Lipocalin-2 has not been previously linked to uterine cancer. Lipocalin-2 represents a interesting marker because of several features. Lipocalins are extracellular carriers of lipophilic molecules such as retinoids, steroids, and fatty acid, all of which may play important roles in the regulation of epithelial cell growth. In addition, because lipocalin is a secreted protein, it may play a role in the regulation of cell proliferation and survival. Of interest, two recent publications on gene expression profiling of breast and pancreatic cancer have proposed lipocalin-2 as a novel therapeutic and diagnostic marker for prevention and treatment of these diseases. The present invention indicates that lipocalin-2 may be added to the known markers for uterine serous papillary carcinoma.

Claudin-3 and Claudin-4

Genes encoding tight junction proteins claudin-3 and claudin-4 were consistently found as two of the most highly up-regulated genes in uterine serous papillary carcinoma with over 8 and 12-fold up-regulation, respectively. Claudin-3 and claudin-4 overexpression have not been previously liked to uterine serous papillary carcinoma. Although the exact function of claudin-3 and claudin-4 in uterine serous papillary carcinoma is still unclear, claudin-3 and claudin-4 have recently been shown to represent the epithelial receptors for *Clostridium perfringens* enterotoxin (CPE), and to be the only family members of the transmembrane tissue-specific claudin proteins capable of mediating CPE binding and cytolysis. Because CPE may trigger a multistep mechanism leading to efficient lysis of mammalian target cells overexpressing claudin-3 and claudin-4, CPE-mediated therapy might be a novel, potentially highly effective strategy for the treatment of uterine serous papillary carcinoma refractory to chemotherapy as well as other human tumors overexpressing claudin-3 and/or claudin-4. Consistent with this view, treatment-resistant prostate cancer and pancreatic cancer, two human malignancies characterized by an extremely poor prognosis, have already been shown to be potentially responsive in vitro as well as in vivo to CPE-mediated therapy. Protein expression data obtained by immunohistochemistry with anti-claudin-4 antibody on uncultured uterine serous papillary carcinoma blocks further support this view.

Kallikrein 6 and Kallikrein 10

The organization of kallikreins, a gene family now consisting of 15 genes which encode for trypsin-like or chymotrypsin-like serine proteases, has been recently elucidated. Serine proteases have been described to have well characterized roles in diverse cellular activities, including blood coagulation, wound healing, digestion, and immune responses, as well as tumor invasion and metastasis. Importantly, because of the secreted nature of some of these enzymes, prostate-specific antigen (PSA) and kallikrein 2 have already found important clinical application as prostate cancer biomarkers. Of interest, kallikrein 6 (also known as zyme/protease M/neurosin) and kallikrein-10 (NES1), two serine proteases recently shown to be present at high levels in the circulation of a subset of ovarian cancer patients, were found to be highly differentially expressed in uterine serous papillary carcinoma when compared to normal endometrial epithelial cells. Both kallikrein 6 and kallikrein 10 overexpression have been shown to correlate with intrinsic resistance to adjuvant chemotherapy and with poor prognosis in ovarian cancer patients. These data are thus consistent with the results presented herein showing high expression of kallikreins 6 and kallikrein 10 in uterine serous papillary carcinoma, a variant of endometrial carcinoma characterized by an aggressive biologic behavior and an inborn resistance to chemotherapy. Importantly, these results further emphasize the view that kallikreins 6 and kallikrein 10 have the potential to become novel cancer markers for early diagnosis and/or monitoring of uterine serous papillary carcinoma as well as possible immunotherapeutic targets of vaccination strategies against recurrent/refractory serous papillary gynecologic tumors.

c-erbB2 c-erbB2 gene was found to be one of the most highly differentially expressed genes in uterine serous papillary carcinoma with over 14-fold up-regulation compared with normal endometrial epithelial cells. Furthermore, the growth factor receptor-bound protein 7 (GRB7), a gene tightly linked to c-erbB2 and previously reported to be co-amplified and co-expressed with this gene in several cancer types, was also highly differentially expressed in uterine serous papillary carcinoma compared to normal endometrial epithelial cells. These data are in agreement with recent discovery of a striking overexpression of the c-erbB2 gene as well as of its gene expression product HER2/neu on 60 to 80% of pure uterine serous papillary carcinoma. Therefore, HER2/neu overexpression may represent a distinctive molecular marker for this highly aggressive subset of endometrial tumors. Over-expression of the c-erbB2 gene on uterine serous papillary carcinoma provides support for the notion that trastuzumab (Herceptin™, Genentech, San Francisco, Calif.), a humanized anti-HER-2/Neu antibody that is showing great promise for treatment of metastatic breast cancer patients overexpressing HER-2/Neu protein, may be a novel and potentially highly effective therapy against this aggressive variant of serous papillary carcinomas. Consistent with this view, uses of Herceptin™ in uterine serous papillary carcinoma patients have been reported with high sensitivity of uterine serous papillary carcinoma to the killing activity mediated by natural killer cells when triggered by anti-HER-2/Neu-specific antibody.

L1 Adhesion Molecule

L1 adhesion molecule (L1CAM), a 200-220 kD type I membrane glycoprotein of the immunoglobulin family, has been shown to play an important function in the development of nervous system by regulating cell adhesion and migration. Although initially characterized and most extensively studied in the nervous system, L1CAM has been recently reported to be expressed on a variety of human tumor cell lines such as neuroblastomas, melanomas, and lung carcinomas. Because overexpression of L1CAM by tumor cells may enhance cell migration on various extracellular membrane substrates, this molecule has been suggested to play a crucial role in the adhesion and migration events crucial for tumor spreading. Data presented herein indicate that L1CAM is one of the most highly differentially expressed genes in uterine serous papillary carcinoma with over 25-fold up-regulation relative to normal endometrial epithelial cells. These data, together with the results presented below, further support using L1CAM as a novel biomarker for predicting clinical outcome in uterine serous papillary carcinoma patients.

Urokinase Plasminogen Activator Receptor

Urokinase plasminogen activator receptor (UPAR) is a glycosyl-phosphatidylinositol-anchored glycoprotein whose role in promoting tumor cell invasion and metastases has been well established in a number of experimental studies. Consistent with this view, urokinase plasminogen activator receptor has been shown to regulate membrane-associated plasmin activity, facilitating cellular movement for tumor-cell invasion, chemotaxis, and cellular adhesion in a variety of human tumors. Furthermore, a direct correlation between urokinase plasminogen activator receptor expression and a higher invasive and metastatic potential in several human tumors has been previously reported. However, it is only recently that an abnormal urokinase plasminogen activator receptor expression in endometrial cancer has been positively correlated with the grade of disease, and in particular, with uterine serous papillary carcinoma phenotype. The present gene expression profiling results show that urokinase plasminogen activator receptor is one of the most highly differentially expressed genes in uterine serous papillary carcinoma with over 7-fold up-regulation relative to normal endometrial epithelial cells. Of interest, because urokinase plasminogen activator receptor protein exists in two forms, as the glycosyl-phosphatidylinositol-anchored glycoprotein (50-60 kDa) present on cell surface, and as a soluble form of UPAR (sUPAR) produced after cleavage of urokinase plasminogen activator receptor by urokinase (35 kDa), measurement of urokinase plasminogen activator receptor levels by ELISA, in analogy to breast cancer, may have potential as prognostic marker to identify early recurrences in endometrial cancer patients associated with poor outcome. Finally, the recent demonstration of urokinase plasminogen activator receptor as a suitable cancer target for both therapeutic and diagnostic application by specific antibody directed against its ligand binding domain may provide a foundation for developing a new type-specific therapy against this highly aggressive disease.

Down-Regulated Genes

The present invention identifies a large number of down-regulated (at least 5-fold) genes in uterine serous papillary carcinoma versus normal endometrial epithelial cells. These genes include transforming growth factor beta receptor III, platelet-derived growth factor receptor alpha, SEMACAP3, ras homolog gene family member I (ARHI), and differentially downregulated in ovarian carcinoma 1 (DOC1). Some of these genes are tumor suppressor genes such as SEMACAP3, ARHI, and DOC1, whereas others encode for proteins important for tissue homeostasis or that have been previously implicated in apoptosis, proliferation, adhesion or tissue maintenance.

In conclusion, multiple uterine serous papillary carcinoma-restricted markers have been identified in the present invention. The identification of HER2/neu and *Clostridium perfringens* enterotoxin epithelial receptors as some of the most highly differentially expressed genes in uterine serous papillary carcinoma when compared to normal endometrial epithelial cells suggest that therapeutic strategies targeting HER2/neu by monoclonal antibodies or claudin 3 and claudin 4 by local and/or systemic administration of *Clostridium Perfringens* enterotoxin may represent novel potentially effective modalities for the treatment of patients harboring this highly aggressive and chemotherapy-resistant variant of endometrial cancer.

Thus, the present invention provides a method of detecting ovarian serous papillary carcinoma. The method involves performing statistical analysis on the expression levels of a group of genes listed in Table 2. Included in this group of genes are plasminogen activator inhibitor-2, fibroblast growth factor receptor-2, glypican 1, lysophosphatidic acid receptor, phospholipase C, glucose-6-phosphate dehydrogenase, and insulin receptor. Over-expression of these genes would indicate that such individual has ovarian serous papillary carcinoma. Gene expression can be examined by a number of standard techniques in the art, e.g. DNA microarray and hierarchical cluster analysis. In general, gene expression can be examined at the protein or RNA level.

In another embodiment of the present invention, there is provided a method of detecting uterine serous papillary carcinoma based on overexpression of a group of genes listed in Tables 3 and 5. Included in these group of genes are epidermal growth factor type 2 receptor, inhibin, multiple endocrine neoplasia, growth factor receptor-bound protein 7, BCL2 E-cadherin, syndecan, cyclin-dependent kinase inhibitor 2A, lipocalin-2, L1 cell adhesion molecule (L1CAM), claudin 3, claudin-4, kallikrein 6 (protease M), kallikrein 10, interleukin-6, interleukin-18, and urokinase plasminogen activator receptor (UPAR).

In another embodiment of the present invention, there is provided a method of detecting uterine serous papillary carcinoma based on down-regulation of a group of genes listed in Table 6. Included in this group of genes are transforming growth factor beta receptor III, platelet-derived growth factor receptor alpha, SEMACAP3, ras homolog gene family member I (ARHI), and differentially down-regulated in ovarian carcinoma 1 (DOC1).

In yet another embodiment of the present invention, there is provided a method of treating uterine serous papillary carcinoma by inhibiting the expression or function of epidermal growth factor type 2 receptor (c-erbB2). In general, inhibition of gene expression can be obtained using anti-HER2/neu antibody or anti-sense oligonucleotide according to standard protocols generally available in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Establishment of Ovarian Serous Papillary Cancer and Uterine Serous Papillary Carcinoma Primary Cell Lines Eleven primary serous papillary cell lines (6 ovarian serous papillary carcinoma and 5 uterine serous papillary carcinoma) were established after sterile processing of the tumor samples from surgical biopsies. Tumors were staged according to the F.I.G.O. operative staging system. Total abdominal hysterectomy and regional lymph node sampling for invasive uterine serous papillary carcinoma were performed in all cases. Radical tumor debulking including a total abdominal hysterectomy and omentectomy, was performed in all ovarian carcinoma patients. No patient received chemotherapy before surgical therapy. The patient characteristics are described in Table 1. The epithelial nature and the purity of uterine serous papillary carcinoma and ovarian serous papillary carcinoma cultures was verified by immunohistochemical staining and flow cytometric analysis with antibodies against cytokeratin as described (Ismail et al., 2000; Satin et al., 2000, 2002). Only primary cultures which had at least 90% viability and contained >99% tumor cells were used for total RNA extraction.

TABLE 1

Characteristics of Patients Disclosed In Example 1

| Patient | Age | Race | Stage | Chemotherapy regimen |
|---|---|---|---|---|
| USPC 1 | 66 | Afro-American | IV B | TAX + CARB |
| USPC 2 | 77 | White | III C | TAX + CARB |
| USPC 3 | 61 | Afro-American | III C | TAX + CARB |

TABLE 1-continued

Characteristics of Patients Disclosed In Example 1

| Patient | Age | Race | Stage | Chemotherapy regimen |
|---|---|---|---|---|
| USPC 4 | 62 | Afro-American | III C | TAX + CARB |
| USPC 5 | 63 | Afro-American | III C | TAX + CARB |
| OSPC 1 | 42 | White | III C | TAX + CIS |
| OSPC 2 | 43 | White | III C | TAX + CARB |
| OSPC 3 | 34 | White | III C | TAX + CARB |
| OSPC 4 | 51 | White | III C | TAX + CARB |
| OSPC 5 | 59 | Afro-American | III B | TAX + CARB |
| OSPC 6 | 52 | White | III C | TAX + CARB |

USPC, Uterine Serous Papillary Carcinoma;
OSPC, Ovarian Serous Papillary Carcinoma.

Example 2

Microarray Hybridization and Analysis

RNA purification, cDNA synthesis, cRNA preparation, and hybridization to the Affymetrix Human U95Av2 Gene-Chip microarray were performed according to the manufacturer's protocols and as reported (Zhan et al., 2002).

All data used in the analyses were derived from Affymetrix 5.0 software. GeneChip 5.0 output files are given as a signal that represents the difference between the intensities of the sequence-specific perfect match probe set and the mismatch probe set, or as a detection of present, marginal, or absent signals as determined by the GeneChip 5.0 algorithm. Gene arrays were scaled to an average signal of 1500 and then analyzed independently. Signal calls were transformed by the log base 2 and each sample was normalized to give a mean of 0 and variance of 1.

Statistical analyses of the data were performed with the software package SPSS10.0 (SPSS, Chicago, Ill.). The first test applied was the detection. In each comparison, genes having "present" detection calls in more than half of the samples in the overexpressed gene group were retained. To compare gene expression levels, the nonparametric Wilcoxon rank sum (WRS) test ($p<0.05$) was applied to the normalized signal call. By combining the detection and WRS data, differentially expressed genes were identified between ovarian serous papillary carcinoma and uterine serous papillary carcinoma.

The hierarchical clustering of average-linkage method with the centered correlation metric was used (Eisen et al., 1998). The dendrogram was constructed with a subset of genes from 12,588 probe sets present on the microarray, whose expression levels vary the most among the 11 samples, and thus most informative. For the hierarchical clustering shown in FIG. 1 and FIG. 2, only genes significantly expressed and whose average change in expression level was at least two-fold were chosen. The expression value of each selected gene was re-normalized to have a mean of zero.

Example 3

Gene Expression Profiles Distinguish Ovarian Serous Papillary Carcinoma from Uterine Serous Papillary Carcinoma Flash frozen biopsies from ovarian and uterine tumor tissue are known to contain significant numbers of contaminant stromal cells as well as a variety of host derived immune cells (e.g., monocytes, dendritic cells, lymphocytes). Short term primary tumor cell cultures minimize the risk of a selection bias inherent in any long term in vitro growth and provide an opportunity to study differential gene expression between relatively pure populations of tumor cells. Thus, comprehensive gene expression profiles of 6 primary ovarian serous papillary carcinoma and 5 primary uterine serous papillary carcinoma cell lines were generated using high-density oligonucleotide arrays with 12,588 probe sets, which in total interrogated some 10,000 genes. One hundred sixty five genes were differentially expressed between ovarian serous papillary carcinoma and uterine serous papillary carcinoma (WRS test, $p<0.05$).

FIG. 1 shows the cluster analysis performed on hybridization intensity values for 59 gene segments whose average difference in expression level was at least two-fold. Two major branches on the dendrogram were identified. All 5 uterine serous papillary carcinoma were grouped together in the leftmost columns. Similarly, in the rightmost columns all 5 pure ovarian serous papillary carcinoma were found to cluster tightly together. Of interest, OSPC2, a serous papillary tumor with mixed clear cell features (i.e., a biologically aggressive variant of ovarian cancer characterized by a poor prognosis) clustered on a sub-branch with uterine serous papillary carcinoma (FIG. 1).

Figure 2:
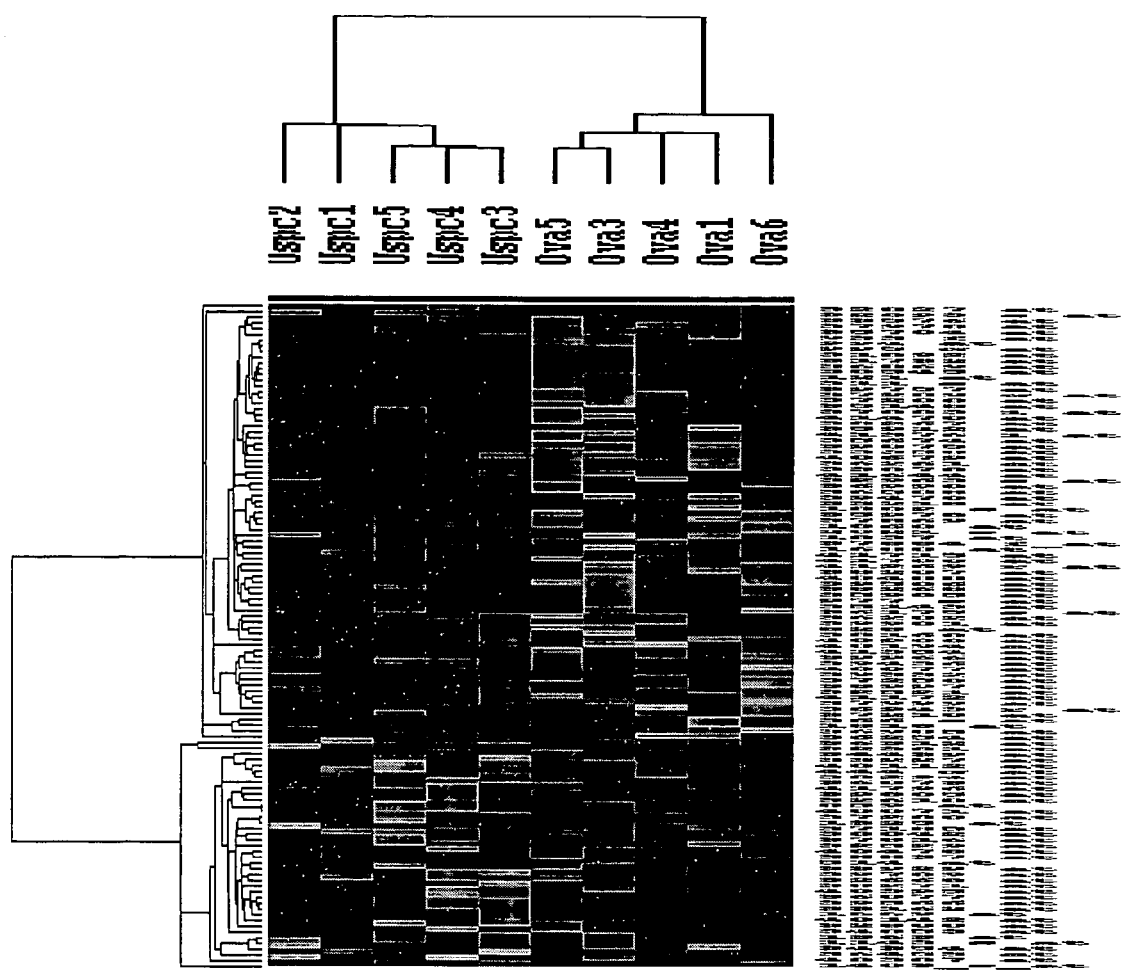
FIG. 2 shows hierarchical clustering of 116 genes with differential expression between 5 ovarian serous papillary cancer and 5 uterine serous papillary carcinoma groups (P<0.05) using a two-fold threshold. The cluster is color-coded using red for up-regulation, green for down-regulation, and black for median expression. Agglomerative clustering of genes was illustrated with dendrograms. The symbol for each gene is followed by the Affymetrix clone number of the corresponding oligonucleotide spotted on the array. Expression ratios comparing each of the two groups to each other are listed.

FIG. 2 shows the cluster analysis on hybridization intensity values for each gene in ten primary cultures of ovarian serous papillary carcinoma and uterine serous papillary carcinoma. By combining the detection levels of genes significantly expressed in ovarian serous papillary carcinoma and uterine serous papillary carcinoma, 227 genes were differentially identified between the two cancer types using the nonparametric WRS test ($p<0.05$). The dendrogram shown in FIG. 2 depicts a marked separation in the expression profiles of the two groups of serous papillary tumors, with 116 gene segments whose average change in expression level was at least two-fold.

The tight clustering of pure ovarian serous papillary carcinoma from uterine serous papillary carcinoma was "driven" by two distinct profiles of gene expression. The first was represented by a group of 40 genes that were highly expressed in ovarian serous papillary carcinoma and underexpressed in uterine serous papillary carcinoma (Table 2). Many genes shown previously to be involved in ovarian carcinogenesis are present on these lists, providing a degree of validity to our array analysis. Included in this group of genes are plasminogen activator inhibitor-2 (PAI-2), fibroblast growth factor receptor-2 (FGFR2), glypican 1 (GPC1), lysophosphatidic acid receptor (EDG2), phospholipase C (PLCL2), glucose-6-phosphate dehydrogenase (G6PD), and insulin receptor (IGF1) (Table 2).

The second profile was represented by 76 genes that were highly expressed in uterine serous papillary carcinoma and underexpressed in ovarian serous papillary carcinoma (Table 3). Included in this group of genes are epidermal growth factor type 2 receptor (c-erbB2), inhibin (INHBB), multiple endocrine neoplasia I (MEN1), growth factor receptor-bound protein 7 (GRB7), BCL2, E-cadherin (CDH1), and syndecan (SDC2) (Table 3). Importantly, c-erbB2 gene was the most highly differentially expressed gene in uterine serous papillary carcinoma when compared to ovarian serous papillary carcinoma (Table 3, FIG. 2). OSPC2, the only serous tumor with mixed clear cell histology evaluated in the series, was also found to highly overexpress c-erbB2.

TABLE 2

Upregulated Genes Expressed At Least 2 Fold Higher In Ovarian Serous Papillary Carcinoma Compared With Uterine Serous Papillary Carcinoma

| Probe Set Name | Gene Symbol | Map Location | p of WRS | Ratio Ov/Ut |
|---|---|---|---|---|
| 37185_at | SERPINB2 | 18q21.3 | 0.00902344 | 21.2101742 |
| 40478_at | DJ971N18.2 | 20p12 | 0.0162936 | 7.391447995 |
| 38837_at | DJ971N18.2 | 20p12 | 0.047201768 | 6.933671714 |
| 34439_at | AIM2 | 1q22 | 0.00902344 | 6.689727463 |
| 36073_at | NDN | 15q11.2-q12 | 0.028280124 | 6.460327167 |
| 859_at | CYP1B1 | 2p21 | 0.047201768 | 4.642443935 |
| 40387_at | EDG2 | 9q32 | 0.047201768 | 4.612620508 |
| 1669_at | WNT5A | 3p21-p14 | 0.028280124 | 4.35214472 |
| 1363_at | FGFR2 | 10q26 | 0.0162936 | 3.958060853 |
| 1143_s_at | | | 0.028280124 | 3.948020982 |
| 37816_at | C5 | 9q32-q34 | 0.0162936 | 3.945622621 |
| 40071_at | CYP1B1 | 2p21 | 0.047201768 | 3.826875845 |
| 38294_at | HOXD4 | 2q31-q37 | 0.028280124 | 3.804399853 |
| 33162_at | INSR | 19p13.3-p13.2 | 0.047201768 | 3.772 |
| 34853_at | FLRT2 | 14q24-q32 | 0.047201768 | 3.471204819 |
| 40395_at | PLXNA2 | 1q32.1 | 0.028280124 | 3.371729137 |
| 39805_at | ABCB6 | 2q36 | 0.047201768 | 3.369062784 |
| 41796_at | PLCL2 | 3p24.3 | 0.00902344 | 3.280007364 |
| 1403_s_at | SCYA5 | 17q11.2-q12 | 0.047201768 | 3.158368265 |
| 33929_at | GPC1 | 2q35-q37 | 0.028280124 | 3.15594993 |
| 39566_at | CHRNA7 | 15q14 | 0.047201768 | 3.14079953 |
| 34354_at | FGFR2 | 10q26 | 0.047201768 | 2.928346342 |
| 444_g_at | HOXD4 | 2q31-q37 | 0.047201768 | 2.892672123 |
| 38042_at | G6PD | Xq28 | 0.047201768 | 2.813117012 |
| 36077_at | RABL4 | 22q13.1 | 0.028280124 | 2.720984156 |
| 36453_at | KIAA0711 | 8p23.3 | 0.047201768 | 2.688792044 |
| 32668_at | SSBP2 | 5q14.1 | 0.047201768 | 2.663148439 |
| 32610_at | RIL | 5q31.1 | 0.047201768 | 2.55031145 |
| 514_at | CBLB | 3q13.12 | 0.028280124 | 2.511893491 |
| 40112_at | IDH3B | 20p13 | 0.028280124 | 2.294973901 |
| 38271_at | HDAC4 | 2q37.2 | 0.028280124 | 2.245891142 |
| 1325_at | MADH1 | 4q28 | 0.047201768 | 2.228503651 |
| 32381_at | RORB | 9q22 | 0.028280124 | 2.205852674 |
| 32800_at | RXRA | 9q34.3 | 0.047201768 | 2.168594631 |
| 36312_at | SERPINB8 | 18q21.3 | 0.047201768 | 2.110497544 |
| 40142_at | DDX24 | 14q32 | 0.0162936 | 2.109997452 |
| 33227_at | IL10RB | 21q22.11 | 0.047201768 | 2.082986437 |
| 32529_at | CKAP4 | 12q23.3 | 0.047201768 | 2.04858844 |
| 37280_at | MADH1 | 4q28 | 0.028280124 | 2.044781456 |
| 39709_at | SEPW1 | 19q13.3 | 0.028280124 | 2.017195806 |

TABLE 3

Upregulated Genes Expressed At Least 2 Fold Higher In Uterine Serous Papillary Carcinoma Compared With Ovarian Serous Papillary Carcinoma

| Probe Set Name | Gene Symbol | Map Location | p of WRS | Ratio Ut/Ov |
|---|---|---|---|---|
| 1802_s_at | ERBB2 | 17q11.2-q12 | 0.028280124 | 17.39166248 |
| 39470_at | | | 0.00902344 | 14.13960749 |
| 41470_at | PROML1 | 4p15.33 | 0.00902344 | 11.00274366 |
| 32521_at | SFRP1 | 8p12-p11.1 | 0.047201768 | 10.49619245 |
| 33218_at | ERBB2 | 17q11.2-q12 | 0.0162936 | 9.009761458 |
| 41354_at | STC1 | 8p21-p11.2 | 0.0162936 | 7.780569927 |
| 41700_at | F2R | 5q13 | 0.028280124 | 7.299013748 |
| 38207_at | MEN1 | 11q13 | 0.028280124 | 6.578419265 |
| 36254_at | TAC1 | 7q21-q22 | 0.047201768 | 6.292979547 |
| 38268_at | SLC1A1 | 9p24 | 0.0162936 | 5.506571087 |
| 33576_at | KIAA0918 | 13q31.1 | 0.0162936 | 5.478319783 |
| 37883_i_at | AF038169 | 2q22.1 | 0.0162936 | 5.06566416 |
| 35704_at | HRASLS3 | 11q13.1 | 0.028280124 | 4.596441783 |
| 38267_at | SLC1A1 | 9p24 | 0.028280124 | 4.488128886 |
| 41376_i_at | UGT2B7 | 4q13 | 0.047201768 | 4.418941048 |
| 828_at | PTGER2 | 14q22 | 0.028280124 | 4.338041431 |
| 39506_at | | | 0.028280124 | 4.313685637 |
| 1680_at | GRB7 | 17q12 | 0.047201768 | 4.262623744 |
| 38545_at | INHBB | 2cen-q13 | 0.028280124 | 4.198823428 |
| 40679_at | SLC6A12 | 12p13 | 0.047201768 | 3.956969879 |
| 35912_at | MUC4 | 3q29 | 0.028280124 | 3.94095027 |
| 39966_at | CSPG5 | 3p21.3 | 0.047201768 | 3.918103678 |
| 32027_at | PDZK1 | 1q21 | 0.047201768 | 3.91484375 |
| 31732_at | RLN2 | 9p24.1 | 0.0162936 | 3.913095715 |
| 36202_at | PKIA | 8q21.11 | 0.047201768 | 3.89984472 |
| 37978_at | QPRT | 16q13 | 0.0162936 | 3.845374532 |
| 994_at | PTPRM | 18p11.2 | 0.047201768 | 3.812843137 |
| 37208_at | PSPHL | 7q11.2 | 0.028280124 | 3.654717567 |
| 37884_f_at | AF038169 | 2q22.1 | 0.028280124 | 3.593346825 |
| 995_g_at | PTPRM | 18p11.2 | 0.028280124 | 3.555706062 |
| 35985_at | AKAP2 | 9q31-q33 | 0.028280124 | 3.319448607 |
| 32963_s_at | RAGD | 6q15-q16 | 0.00902344 | 3.280777993 |
| 33358_at | KIAA1157 | 12q13.13 | 0.0162936 | 3.250881457 |
| 311_s_at | | | 0.0162936 | 3.138465417 |
| 35674_at | PADI2 | 1p35.2-p35.1 | 0.047201768 | 3.100307522 |
| 2021_s_at | CCNE1 | 19q12 | 0.028280124 | 3.081090355 |
| 32893_s_at | GGT2 | 22q11.23 | 0.047201768 | 3.055014721 |
| 36869_at | PAX8 | 2q12-q14 | 0.047201768 | 3.050015496 |
| 36508_at | GPC4 | Xq26.1 | 0.0162936 | 2.887073572 |
| 39901_at | MYO7A | 11q13.5 | 0.028280124 | 2.885983264 |
| 35148_at | TJP3 | 19p13.3 | 0.028280124 | 2.879832572 |

TABLE 3-continued

Upregulated Genes Expressed At Least 2 Fold Higher In Uterine Serous
Papillary Carcinoma Compared With Ovarian Serous Papillary Carcinoma

| Probe Set Name | Gene Symbol | Map Location | p of WRS | Ratio Ut/Ov |
|---|---|---|---|---|
| 31892_at | PTPRM | 18p11.2 | 0.047201768 | 2.844557651 |
| 36990_at | UCHL1 | 4p14 | 0.0162936 | 2.833524684 |
| 37209_g_at | PSPHL | 7q11.2 | 0.047201768 | 2.780479031 |
| 38168_at | INPP4B | 4q31.1 | 0.00902344 | 2.645321215 |
| 36943_r_at | PLAGL1 | 6q24-q25 | 0.0162936 | 2.57527834 |
| 37258_at | TMEFF1 | 9q31 | 0.047201768 | 2.55946924 |
| 36985_at | IDI1 | 10p15.3 | 0.047201768 | 2.538587569 |
| 39075_at | NEU1 | 6p21.3 | 0.0162936 | 2.521110072 |
| 40488_at | DMD | Xp21.2 | 0.00902344 | 2.507697552 |
| 39332_at | TUBB | 6p21.3 | 0.047201768 | 2.504487188 |
| 39757_at | SDC2 | 8q22-q23 | 0.047201768 | 2.452025072 |
| 933_f_at | ZNF91 | 19p13.1-p12 | 0.028280124 | 2.445525292 |
| 37210_at | INA | 10q25.1 | 0.047201768 | 2.387532735 |
| 1860_at | TP53BP2 | 1q42.1 | 0.0162936 | 2.356857655 |
| 37869_at | ELKS | 12p13.3 | 0.028280124 | 2.356300578 |
| 33878_at | FLJ13612 | 2q36.1 | 0.0162936 | 2.319659881 |
| 35143_at | DKFZP566A1524 | | 0.047201768 | 2.312331476 |
| 38997_at | SLC25A1 | 22q11.21 | 0.00902344 | 2.304275318 |
| 40077_at | ACO1 | 9p22-p13 | 0.028280124 | 2.297124855 |
| 36261_at | LOC51760 | 16p13.13 | 0.028280124 | 2.252602915 |
| 39436_at | BNIP3L | 8p21 | 0.047201768 | 2.236567978 |
| 977_s_at | CDH1 | 16q22.1 | 0.00902344 | 2.212331718 |
| 36175_s_at | HIVEP2 | 6q23-q24 | 0.047201768 | 2.206300362 |
| 41269_r_at | API5 | 11p12-q12 | 0.0162936 | 2.189353711 |
| 1837_at | | | 0.047201768 | 2.180124558 |
| 1818_at | | | 0.047201768 | 2.177494716 |
| 366_s_at | NEK2 | 1q32.2-q41 | 0.047201768 | 2.157771457 |
| 40900_at | | | 0.028280124 | 2.151464435 |
| 40194_at | | | 0.028280124 | 2.133081444 |
| 41172_at | ARSDR1 | 14q23.3 | 0.0162936 | 2.113388456 |
| 37999_at | CPO | 3q12 | 0.028280124 | 2.100322069 |
| 35978_at | PRRG1 | Xp21.1 | 0.028280124 | 2.05552932 |
| 121_at | PAX8 | 2q12-q14 | 0.028280124 | 2.028946437 |
| 41715_at | PIK3C2B | 1q32 | 0.00902344 | 2.024856688 |
| 41644_at | KIAA0790 | 6q24.3 | 0.047201768 | 2.004743183 |

Example 4

Quantitative Real Time PCR Analysis of PAI-2 and c-erbB2 Expression

Quantitative real time PCR assays were used to validate the microarray data. The two most highly differentially expressed genes between uterine serous papillary carcinoma and ovarian serous papillary carcinoma (i.e., PAI-2 and c-erbB2) were selected for the analysis.

Quantitative real time PCR was performed with an ABI Prism 7000 Sequence Analyzer using the manufacturer's recommended protocol (Applied Biosystems, Foster City, Calif.). Each reaction was run in triplicate. The comparative threshold cycle ($C_T$) method was used for the calculation of amplification fold as specified by the manufacturer. Briefly, five mg of total RNA from each sample was reverse transcribed using SuperScript II Rnase H Reverse Transcriptase (Invitrogen, Carlsbad, Calif.). Ten ml of reverse transcribed RNA samples (from 500 ul of total volume) were amplified by using the TaqMan™ Universal PCR Master Mix (Applied Biosystems) to produce PCR products specific for PAI-2 and c-erbB2. Primers specific for 18s ribosomal RNA and empirically determined ratios of 18s competitors (Applied Biosystems) were used to control for the amounts of cDNA generated from each sample. Differences among uterine serous papillary carcinoma and ovarian serous papillary carcinoma in the quantitative real time PCR expression data were tested using the Kruskal-Wallis nonparametric test. Pearson product-moment correlations were used to estimate the degree of association between the microarray and quantitative real time PCR data.

Figure 3:
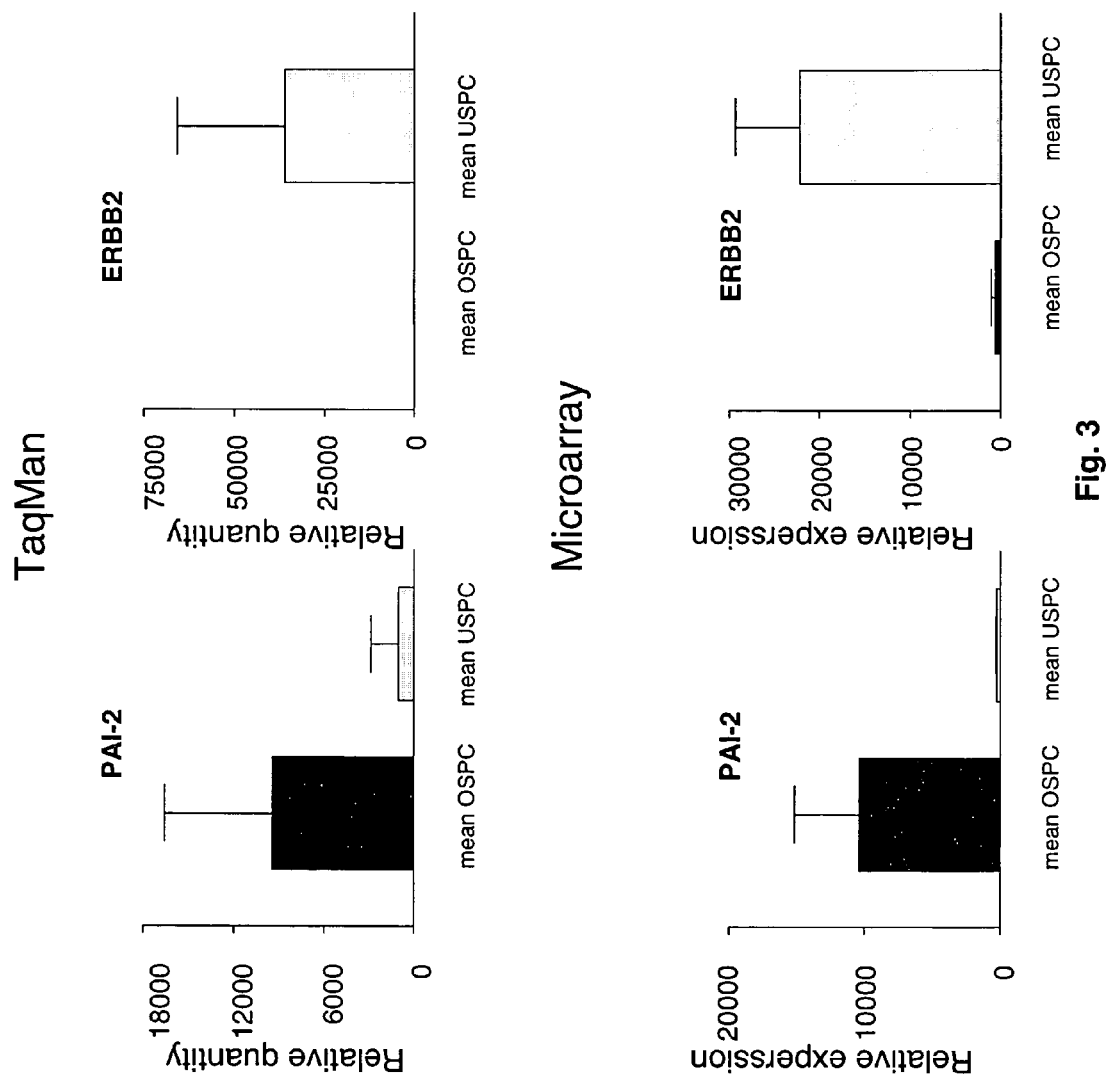
FIG. 3 shows quantitative real-time PCR and microarray expression analysis of PAI-2 (SERPINB2) and c-erbB2 (ERBB2). These two genes are differentially expressed between ovarian serous papillary cancer and uterine serous papillary carcinoma.

A comparison of the microarray and quantitative real time PCR data for the two genes is shown in FIG. 3. Expression differences between tumor types for PAI-2 (p=0.009) and c-erbB2 (p=0.02) were readily apparent (Table 2 and 3). Moreover, for both genes tested, the quantitative real time PCR data were highly correlated to the microarray data (p<0.001, r=0.91 and 0.71, respectively) as estimated from 6 samples (i.e., 3 uterine serous papillary carcinoma and 3 ovarian serous papillary carcinoma). The quantitative real time PCR data mirror the microarray data both qualitatively and quantitatively, suggesting that most array probe sets are likely to accurately measure the levels of the intended transcript within a complex mixture of transcripts.

Example 5

Flow Cytometry Analysis of HER-2/Neu Expression

To validate microarray data on primary uterine serous papillary carcinoma and ovarian serous papillary carcinoma cell lines at the protein level, HER-2/neu receptor expression was evaluated by flow cytometry on six primary serous papillary cell lines (3 uterine serous papillary carcinoma and 3 ovarian serous papillary carcinoma). The HER-2/neu MAb Herceptin™ (Genentech, San Francisco, Calif.) was used as the primary antibody. FITC-conjugated goat anti-human $F(ab)^2$ immunoglobulin was used as a secondary reagent (BioSource International, Camarillo, Calif.). Analysis was conducted with a FACScan, utilizing Cell Quest software (Becton Dickinson).

Figure 4:
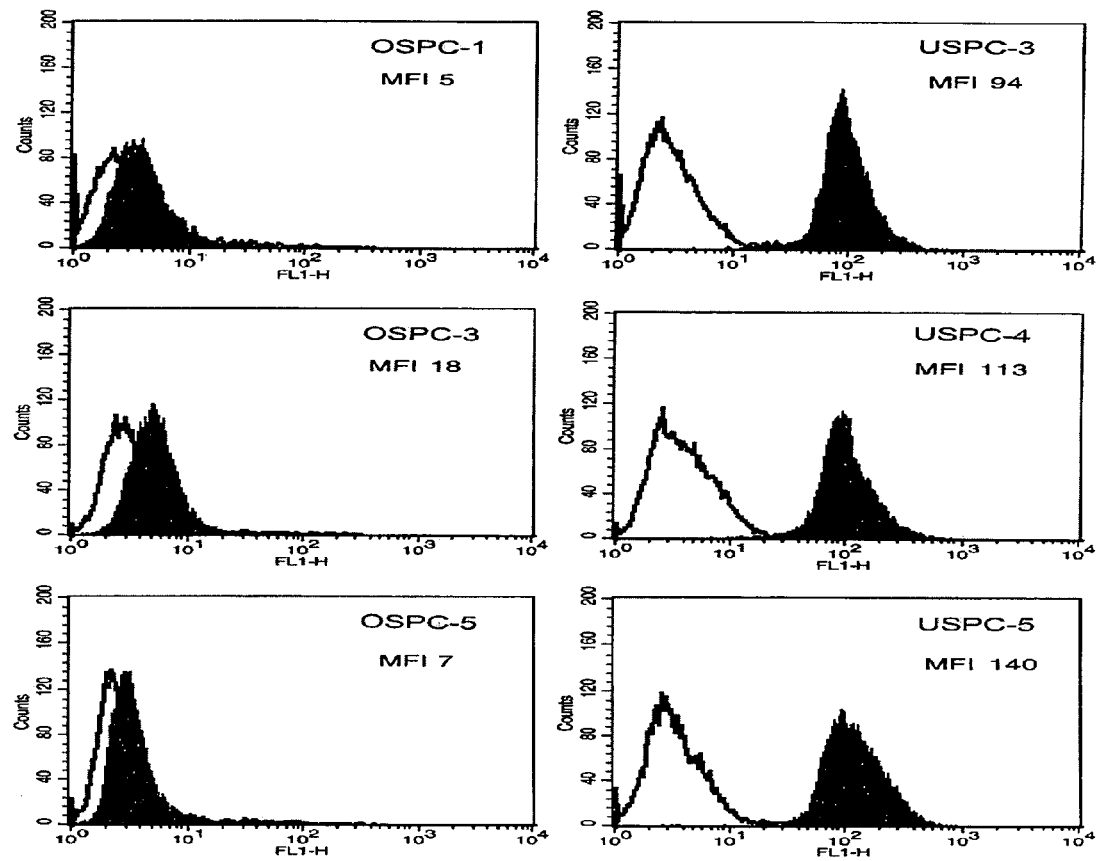
FIG. 4 shows FACS analysis of Herceptin™ staining of 3 primary ovarian serous papillary cancer and 3 uterine serous papillary carcinoma cell lines. Data with Herceptin™ are shown in solid black while isotype control monoclonal antibody profiles are shown in white. HER-2/neu expression was significantly higher on uterine serous papillary carcinoma cell lines compared to ovarian serous papillary cancer cell lines (p<0.001 by student t test).

As positive and negative controls, breast cancer cell lines known to overexpress HER-2/neu (BT-474 and SK-BR-3, American Type Culture Collection), and Epstein-Barr virus-transformed lymphoblastoid cell lines (LCL) established from the same patients were also studied. High HER-2/neu receptor expression was found on all three primary uterine serous papillary carcinoma cell lines tested (100% positive cells for all three cell lines), with mean fluorescence intensity (MFI) ranging from 94 to 140 (FIG. 4). In contrast, primary ovarian serous papillary carcinoma cell lines were found to express significantly lower levels of HER-2/neu (average MFI was ten-fold lower) than the uterine serous papillary carcinoma cells (p<0.001) (FIG. 4). These results show that high expression of the c-erbB2 gene product by uterine serous papillary carcinoma correlates tightly with high protein expression by the tumor cells. Autologous LCL were consistently negative for HER-2/neu expression, while breast cancer cell lines expressed high levels of HER-2/neu (data not shown).

Example 6

Immunohistochemical Analysis of HER2/Neu Expression

Formalin fixed tumor tissue blocks from six primary surgical specimens were tested for HER-2/neu expression by immunohistochemical staining. The intensity of staining was graded as 0 (staining not greater than negative control), 1+ (light staining), 2+ (moderate staining) or 3+ (heavy staining).

Figure 5:
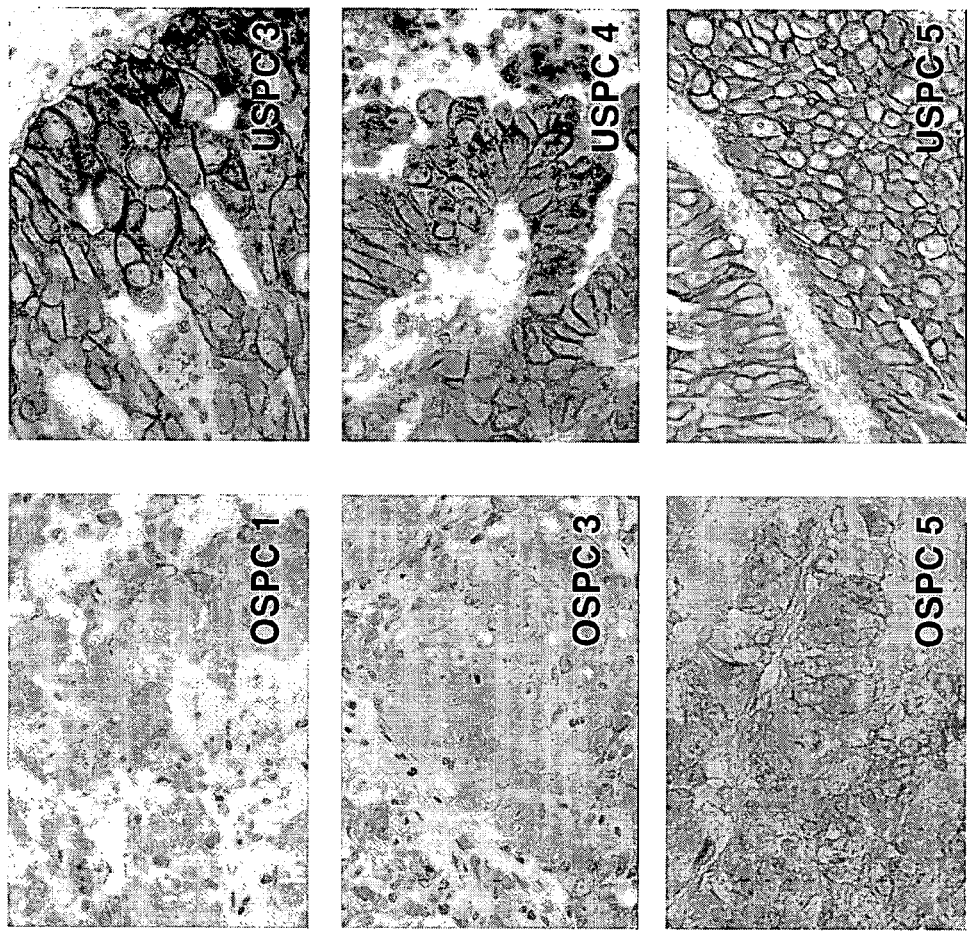
FIG. 5 shows immunohistochemical staining for HER-2/neu expression on 3 paraffin embedded ovarian serous papillary cancer (OSPC) and 3 uterine serous papillary carcinoma (USPC) specimens. OSPC1, OSPC2 and OSPC3 (right panel) showed negative or light (1+) staining for HER-2/neu. USPC1, USPC3, and USPC4 (left panel), showed heavy (3+) staining for HER-2/neu. Original magnification 400×.

Heavy staining for HER-2/neu protein expression (i.e., score 3+) was noted in all three uterine serous papillary carcinoma specimens that also overexpressed the c-erbB2 gene product detected by microarray and flow cytometry (FIG. 5). In contrast, negative or low (i.e., score 0 or 1+) staining was found in all 3 representative ovarian serous papillary carcinoma samples (FIG. 5).

Example 7

Establishing Primary Cell Lines of Uterine Serous Papillary Carcinoma and Normal Endometrial Epithelial Cells A total of fifteen primary cell lines (i.e., 10 uterine serous papillary carcinoma cell lines and 5 normal endometrial epithelial cell lines) were established after sterile processing of samples from surgical biopsies collected from 1997 to 2003. Tumors were staged according to the F.I.G.O. operative staging system. A total abdominal hysterectomy with bilateral salpingo oophorectomy and bilateral pelvic lymphadenectomy was performed in all uterine carcinoma patients while normal endometrial tissue was obtained from consenting donors undergoing surgery for benign pathology. No patient received chemotherapy or radiation before surgery. Patient characteristics are described in Table 4. The cell lines were established as previously described for uterine serous papillary carcinoma specimens (Santin et al., 2002) and normal endometrial epithelial cell cultures (Bongso et al., 1988; Meresman et al., 2003). Briefly, normal tissue was obtained from healthy endometria mechanically minced and enzymatically dissociated with 0.14% collagenase Type I (Sigma, St. Louis, Mo.) in RPMI 1640 as described previously by Bongso et al. (1988) with minor modifications. After 1-2 hrs incubation with enzymes on a magnetic stirring apparatus at 37° C. in an atmosphere of 5% $CO_2$, the resulting suspension was collected by centrifugation at 100 g for 5-10 minutes and washed twice with RPMI 1640 medium (Sigma Chemical Co., St. Louis, Mo.) containing 10% fetal bovine serum (FBS, Invitrogen, Grand Island, N.Y.). The final pellet was then placed in fresh RPMI 1640 medium containing 10% fetal bovine serum (FBS, Invitrogen), 200 U/ml penicillin, and 200 µg/ml streptomycin in tissue culture flasks or Petri dishes (Invitrogen). The epithelial explants were then allowed to attach and proliferate. Explants were trypsinized and subcultured for 1 to 2 passages before being collected for RNA extraction.

Tumor tissue was mechanically minced in RPMI 1640 to portions no larger than 1-3 $mm^3$ and washed twice with RPMI 1640. The portions of minced tumor were then placed into 250 ml flasks containing 30 ml of enzyme solution [0.14% collagenase Type I (Sigma, St. Louis, Mo.) and 0.01% DNAse (Sigma, 2000 KU/mg)] in RPMI 1640, and either incubated on a magnetic stirring apparatus for 1-2 hrs at 37° C. in an atmosphere of 5% $CO_2$ or overnight at 4° C. Enzymatically dissociated tumor was then filtered through 150 mm nylon mesh to generate a single cell suspension. The resultant cell suspension was then washed twice in RPMI 1640 plus 10% FBS. Primary cell lines were maintained in RPMI 1640 supplemented with 10% FBS, 200 U/ml penicillin, 200 µg/ml streptomycin at 37° C., 5% $CO_2$. Some of the primary uterine serous papillary carcinoma cell lines had been cultured in vitro over 2-4 weeks, whereas others had been cultured over a much longer period of time. The epithelial nature and the purity of the cell cultures were verified by immunohistochemical staining and flow cytometric analysis with antibodies against cytokeratin and vimentin as previously described (Santin et al., 2002; Meresman et al., 2003). Only primary cultures which had at least 90% viability and contained >99% epithelial cells were used for total RNA extraction.

TABLE 4

Characteristics of Patients Disclosed In Example 7

| Patient | Age | Race | Stage |
| --- | --- | --- | --- |
| USPC 1 | 65 | White | IV B |
| USPC 2 | 75 | Afro-American | III C |
| USPC 3 | 75 | Afro-American | IV A |
| USPC 4 | 59 | White | IV A |
| USPC 5 | 59 | White | III C |
| USPC 6 | 62 | Afro-American | IV B |
| USPC 7 | 63 | Afro-American | III C |
| USPC 8 | 61 | Afro-American | III C |
| USPC 9 | 78 | White | III C |
| USPC 10 | 64 | Afro-American | IV A |

Example 8

Gene Expression Profiles Distinguish Uterine Serous Papillary Carcinoma from Normal Endometrial Epithelial Cells Tumor tissue flash frozen biopsies are known to contain significant numbers of contaminant stromal cells as well as a variety of host derived immune cells (e.g., monocytes, dendritic cells, lymphocytes). In addition, uterine serous papillary carcinoma represents rare tumors which may present in either pure forms, or admixed with endometrioid or clear cell tumor cells. To minimize the risk of contamination of uterine serous papillary carcinoma RNA with that of normal cells or tumor cells with different histology (i.e., endometrioid or clear cells), as well as to reduce the complexity of gene expression data analysis, RNA was extracted from short term primary tumor cell cultures collected only from uterine serous papillary carcinoma with single type differentiation. Pure uterine serous papillary carcinoma and normal endometrial epithelial cell cultures, minimizing the risk of a selection bias inherent in any long term in vitro growth, provide an opportunity to study differential gene expression between highly enriched populations of normal and tumor-derived epithelial cells.

Accordingly, comprehensive gene expression profiles of 10 primary uterine serous papillary carcinoma cell lines and 5 primary normal endometrial epithelial cell lines were generated using high-density oligonucleotide arrays with 12,533 probe sets, which in total interrogated some 10,000 genes. Statistical analyses of the data were performed with the software packages SPSS10.0 (SPSS, Chicago, Ill.) and the significance analysis of microarrays (SAM) method (Tusher et al., 2001). Genes were selected for analysis based on detection and fold change. In each comparison, genes having "present" detection calls in more than half of the samples in the overexpressed gene group were retained for statistical analysis if they showed >5-fold change between groups. Retained genes were subjected to SAM to establish a false discovery rate, then further filtered via the Wilcoxon rank sum (WRS) test at alpha=0.05. The false discovery rate obtained from the initial SAM analysis was assumed to characterize genes found significant via WRS.

Hierarchical clustering of average-linkage method with the centered correlation metric was used (Eisen et al., 1998). For the unsupervised hierarchical clustering shown in FIG. 6, a total of 7,328 probe sets were scanned across the two groups of primary cultures. The 7,328 probe sets were derived from 12,588 by filtering out all control genes, all genes with absent detections, and genes not fulfilling the test of standard deviation greater than 0.5 (0.5 being the log base 2 of the signal).

Figure 6:
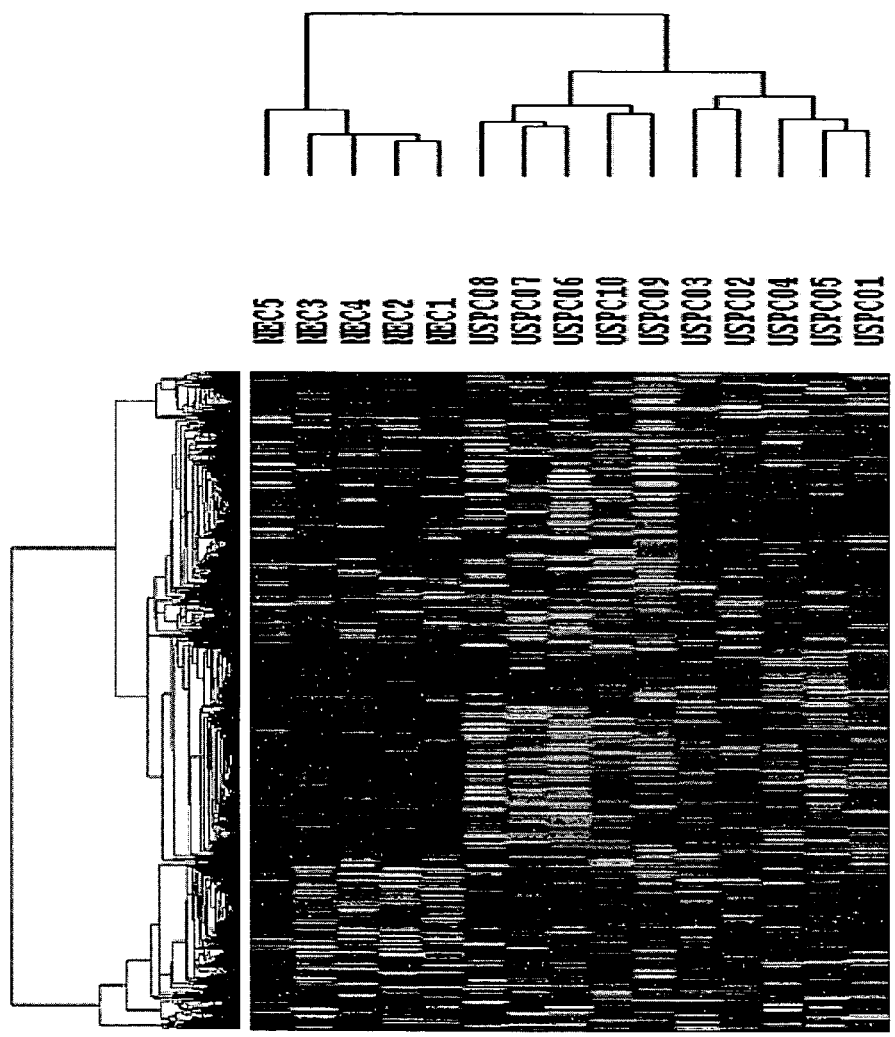
FIG. 6 shows unsupervised hierarchical clustering of fifteen primary uterine cell lines (i.e., 10 uterine serous papillary carcinoma and 5 normal endometrial epithelial cultures). The cluster is color-coded using red for up-regulation, green for down-regulation, and black for median expression. Agglomerative clustering of genes is illustrated with dendrograms.

As shown in FIG. 6, all 10 uterine serous papillary carcinoma cell lines were found to group together in the rightmost columns of the dendrogram. Similarly, in the leftmost columns all 5 normal endometrial epithelial cell lines were found to cluster tightly together. After filter out most "absent" genes, the SAM and the nonparametric WRS test (p<0.05) were performed to identify genes differentially expressed between uterine serous papillary carcinoma and normal endometrial epithelial cells. A total of 2,829 probe sets were found differentially expressed between the two groups with p<0.05 by WRS and with a median false discovery rate of 0.35% and a $90^{th}$ percentile false discovery rate of 0.59% by SAM.

Of the 2,829 aforementioned probe sets, there were 529 probe sets showing >5-fold change. As shown in Table 5, a group of 139 probe sets were found highly expressed in uterine serous papillary carcinoma and underexpressed in normal endometrial epithelial cells. Included in these group of genes are CDKN2A/p16/p14ARF, L1 cell adhesion molecule (L1CAM), claudin 3 and claudin-4, kallikrein 6 (protease M) and kallikrein 10, (SCCE), interleukin-6, interleukin-18 and plasminogen activator receptor (PLAUR). Importantly, c-erbB2, which is highly expressed in uterine serous papillary carcinoma when compared to ovarian serous papillary tumors, was 14-fold more expressed in uterine serous papillary carcinoma when compared to normal endometrial epithelial cells (Table 5).

The second profile was represented by 390 genes that were highly expressed in normal endometrial epithelial cells and underexpressed in uterine serous papillary carcinoma (Table 6). Included in this group of genes are transforming growth factor beta receptor III, platelet-derived growth factor receptor alpha, SEMACAP3, ras homolog gene family, member I (ARHI), and differentially downregulated in ovarian carcinoma 1 (DOC1).

TABLE 5

Upregulated Genes Expressed At Least 5-Fold Higher In Uterine Serous Papillary Carcinoma Compared With Normal Endometrial Epithelial Cells

| Probe Set | Gene Symbol | SAM Score(d) | p of WRS | Ratio USPC/NEC |
|---|---|---|---|---|
| 1713_s_at | CDKN2A | 10.59223007 | 0.0027 | 101.9077377 |
| 36288_at | KRTHB1 | 4.573430656 | 0.0027 | 77.3983986 |
| 33272_at | SAA1 | 3.777977393 | 0.0063 | 45.74937337 |
| 41294_at | KRT7 | 7.173346265 | 0.0027 | 41.46788873 |
| 32154_at | TFAP2A | 7.636996321 | 0.0027 | 32.47929396 |
| 31610_at | MAP17 | 3.621151787 | 0.0093 | 30.28302802 |
| 408_at | — | 4.070053148 | 0.0063 | 30.14111158 |
| 32821_at | LCN2 | 5.126089463 | 0.0027 | 27.69975608 |
| 35174_i_at | EEF1A2 | 2.839620426 | 0.0278 | 26.80482891 |
| 38551_at | L1CAM | 3.115032534 | 0.0196 | 25.60938089 |
| 38249_at | VGLL1 | 5.273984976 | 0.0027 | 24.69495091 |
| 35879_at | GAL | 5.593811144 | 0.0027 | 23.48953559 |
| 36838_at | KLK10 | 3.455062978 | 0.0136 | 23.17518549 |
| 38299_at | IL6 | 3.62957424 | 0.0041 | 19.05873079 |
| 38051_at | MAL | 4.877642645 | 0.0041 | 17.51555106 |
| 41469_at | PI3 | 2.853526521 | 0.0063 | 16.90464558 |
| 40412_at | PTTG1 | 5.218191198 | 0.0027 | 16.61222352 |
| 1886_at | WNT7A | 3.544426758 | 0.0196 | 16.11519778 |
| 33128_s_at | CST6 | 4.221666931 | 0.0136 | 15.97856318 |
| 38414_at | CDC20 | 7.317470579 | 0.0027 | 15.64601435 |
| 34012_at | KRTHA4 | 2.410988057 | 0.0278 | 15.37247475 |
| 37554_at | KLK6 | 3.784630357 | 0.0093 | 15.23781352 |
| 1802_s_at | ERBB2 | 2.566389361 | 0.0136 | 14.52012028 |
| 41060_at | CCNE1 | 6.092165808 | 0.0027 | 14.16647068 |
| 36837_at | KIF2C | 6.129605781 | 0.0027 | 14.1328483 |
| 34213_at | KIBRA | 5.300586641 | 0.0027 | 13.27228177 |
| 1651_at | UBE2C | 5.554093545 | 0.0027 | 12.87617243 |
| 35276_at | CLDN4 | 6.381184288 | 0.0027 | 12.74825421 |
| 36990_at | UCHL1 | 4.623383279 | 0.0027 | 12.30505908 |
| 35977_at | DKK1 | 4.494993915 | 0.0041 | 12.25382636 |
| 36113_s_at | TNNT1 | 4.071523595 | 0.0027 | 11.93824813 |
| 2011_s_at | BIK | 3.451043397 | 0.0063 | 11.66959681 |
| 543_g_at | CRABP1 | 3.193471228 | 0.0093 | 11.55494382 |
| 34852_g_at | STK6 | 6.224691811 | 0.0027 | 11.51812047 |
| 33483_at | NMU | 4.093975777 | 0.0027 | 11.42057993 |
| 39109_at | TPX2 | 6.161639109 | 0.0027 | 11.29208457 |
| 37018_at | HIST1H1C | 2.26997194 | 0.0278 | 10.74270622 |
| 1165_at | IL18 | 3.220966429 | 0.0041 | 10.65596528 |
| 36477_at | TNNI3 | 2.867426116 | 0.0136 | 10.61101382 |
| 572_at | TTK | 3.720282658 | 0.0093 | 9.723902052 |
| 31542_at | FLG | 2.622102112 | 0.0196 | 9.600831601 |
| 35937_at | MICB | 4.238382451 | 0.0093 | 9.460109582 |
| 36155_at | SPOCK2 | 2.277735266 | 0.0278 | 9.216570003 |
| 32186_at | SLC7A5 | 4.148798845 | 0.0063 | 9.121679665 |
| 35766_at | KRT18 | 5.933225457 | 0.0027 | 9.01220054 |
| 35822_at | BF | 3.266560726 | 0.0063 | 8.952514469 |
| 35714_at | PDXK | 6.549900892 | 0.0027 | 8.898191704 |
| 1369_s_at | — | 2.679010624 | 0.0196 | 8.773380878 |
| 40079_at | RAI3 | 4.515766371 | 0.0063 | 8.626843209 |
| 37168_at | LAMP3 | 2.837727959 | 0.0136 | 8.616807346 |
| 39704_s_at | HMGA1 | 5.322233414 | 0.0027 | 8.597894471 |
| 1887_g_at | WNT7A | 3.003097491 | 0.0196 | 8.491813649 |
| 36929_at | LAMB3 | 5.769944566 | 0.0027 | 8.354149098 |
| 527_at | CENPA | 6.125858747 | 0.0027 | 8.32992789 |
| 41081_at | BUB1 | 4.882654417 | 0.0027 | 8.213759056 |
| 885_g_at | ITGA3 | 4.447267172 | 0.0027 | 8.20660555 |
| 2021_s_at | CCNE1 | 4.399072926 | 0.0041 | 8.199388463 |
| 33904_at | CLDN3 | 3.296023945 | 0.0136 | 8.020010794 |
| 33730_at | RAI3 | 4.648262631 | 0.0041 | 7.923899439 |
| 34736_at | CCNB1 | 5.077963775 | 0.0063 | 7.896644626 |
| 757_at | ANXA2 | 3.514460359 | 0.0063 | 7.870466864 |
| 910_at | TK1 | 3.933693732 | 0.0093 | 7.869091533 |
| 34851_at | STK6 | 4.491412407 | 0.0041 | 7.764803777 |
| 34703_f_at | — | 2.275488598 | 0.0278 | 7.710260816 |
| 34715_at | FOXM1 | 5.318031066 | 0.0027 | 7.659023602 |
| 38971_r_at | TNIP1 | 6.799881197 | 0.0027 | 7.595036872 |
| 32263_at | CCNB2 | 4.245537907 | 0.0063 | 7.578513543 |
| 1680_at | GRB7 | 4.013375211 | 0.0027 | 7.471384928 |
| 38247_at | F2RL1 | 3.185259514 | 0.0093 | 7.432476326 |
| 160025_at | TGFA | 6.08814344 | 0.0027 | 7.355344272 |
| 1945_at | CCNB1 | 5.297806506 | 0.0041 | 7.291039832 |
| 31792_at | ANXA3 | 4.872657477 | 0.0041 | 7.266892828 |
| 182_at | ITPR3 | 5.431705752 | 0.0027 | 7.172450367 |

TABLE 5-continued

Upregulated Genes Expressed At Least 5-Fold Higher In Uterine Serous Papillary Carcinoma Compared With Normal Endometrial Epithelial Cells

| Probe Set | Gene Symbol | SAM Score(d) | p of WRS | Ratio USPC/NEC |
|---|---|---|---|---|
| 1117_at | CDA | 2.936875649 | 0.0093 | 7.114518646 |
| 902_at | EPHB2 | 5.186069433 | 0.0027 | 7.065363569 |
| 634_at | PRSS8 | 5.21560703 | 0.0041 | 7.001894703 |
| 41169_at | PLAUR | 3.982498409 | 0.0063 | 7.00139089 |
| 33203_s_at | FOXD1 | 3.4642857 | 0.0093 | 6.989749222 |
| 40095_at | CA2 | 4.285159359 | 0.0027 | 6.946396937 |
| 38940_at | AD024 | 5.064744169 | 0.0041 | 6.928406028 |
| 34348_at | SPINT2 | 6.262957935 | 0.0027 | 6.877224695 |
| 33933_at | WFDC2 | 3.343526736 | 0.0136 | 6.820073691 |
| 35281_at | LAMC2 | 3.346662529 | 0.0093 | 6.7580474 |
| 349_g_at | KIFC1 | 5.275031682 | 0.0041 | 6.700913018 |
| 33218_at | ERBB2 | 2.710053625 | 0.0027 | 6.615105998 |
| 38881_i_at | TRIM16 | 3.000641338 | 0.0196 | 6.506893575 |
| 1536_at | CDC6 | 4.666139295 | 0.0041 | 6.463305623 |
| 38482_at | CLDN7 | 4.930843791 | 0.0041 | 6.409117877 |
| 40697_at | CCNA2 | 3.396480338 | 0.0093 | 6.40768505 |
| 41688_at | TM4SF11 | 4.390330663 | 0.0027 | 6.366861533 |
| 38158_at | ESPL1 | 6.007466409 | 0.0027 | 6.225688779 |
| 38474_at | CBS | 3.379648389 | 0.0093 | 6.212078913 |
| 36483_at | GALNT3 | 3.889728637 | 0.0041 | 6.181109111 |
| 35372_r_at | IL8 | 2.359705895 | 0.0278 | 6.133149591 |
| 41585_at | KIAA0746 | 4.436299723 | 0.0027 | 6.092207586 |
| 36832_at | B3GNT3 | 5.456967667 | 0.0027 | 5.941291793 |
| 1107_s_at | G1P2 | 3.937533177 | 0.0063 | 5.923287019 |
| 35207_at | SCNN1A | 3.076038486 | 0.0136 | 5.920739634 |
| 36863_at | HMMR | 2.830001586 | 0.0196 | 5.905038013 |
| 38631_at | TNFAIP2 | 4.924314508 | 0.0027 | 5.897745642 |
| 36813_at | TRIP13 | 5.665655915 | 0.0027 | 5.870351247 |
| 41048_at | PMAIP1 | 3.489974054 | 0.0062 | 5.853172336 |
| 2084_s_at | ETV4 | 3.742551143 | 0.0093 | 5.798002338 |
| 33245_at | MAPK13 | 3.774897977 | 0.0136 | 5.766618762 |
| 37347_at | CKS1B | 5.542650247 | 0.0027 | 5.762817533 |
| 34282_at | NFE2L3 | 2.668167751 | 0.0136 | 5.734907375 |
| 330_s_at | — | 4.026422371 | 0.0041 | 5.726752495 |
| 41732_at | na | 6.920337146 | 0.0027 | 5.706487141 |
| 1516_g_at | — | 6.725730866 | 0.0027 | 5.63870137 |
| 904_s_at | TOP2A | 3.418887485 | 0.0063 | 5.634251452 |
| 36041_at | EXO1 | 4.970840916 | 0.0027 | 5.59235892 |
| 33143_s_at | SLC16A3 | 4.007293245 | 0.0063 | 5.56591457 |
| 37228_at | PLK | 4.500601808 | 0.0041 | 5.564532365 |
| 1854_at | MYBL2 | 4.116712652 | 0.0063 | 5.54317592 |
| 40407_at | KPNA2 | 4.188947411 | 0.0041 | 5.51635645 |
| 33282_at | LAD1 | 3.904051584 | 0.0063 | 5.509367036 |
| 40145_at | TOP2A | 3.30652637 | 0.0093 | 5.48127065 |
| 1100_at | IRAK1 | 5.530078337 | 0.0027 | 5.470162749 |
| 37883_i_at | AF038169 | 3.159630542 | 0.0027 | 5.460495655 |
| 37343_at | ITPR3 | 5.257721251 | 0.0027 | 5.449013729 |
| 31598_s_at | GALE | 4.646763029 | 0.0027 | 5.442955253 |
| 889_at | ITGB8 | 2.743766192 | 0.0093 | 5.370592815 |
| 37558_at | IMP-3 | 3.122846843 | 0.0093 | 5.364127468 |
| 32715_at | VAMP8 | 5.685902454 | 0.0027 | 5.352873419 |
| 36312_at | SERPINB8 | 3.611288676 | 0.0027 | 5.327343554 |
| 37210_at | INA | 3.550708512 | 0.0063 | 5.307526088 |
| 35699_at | BUB1B | 3.664553007 | 0.0196 | 5.279075308 |
| 32787_at | ERBB3 | 2.657607539 | 0.0041 | 5.247404657 |
| 32275_at | SLPI | 3.726091901 | 0.0041 | 5.221163981 |
| 893_at | E2-EPF | 3.774672918 | 0.0063 | 5.196412396 |
| 41583_at | FEN1 | 5.481105111 | 0.0027 | 5.196005796 |
| 41781_at | PPFIA1 | 4.113488223 | 0.0027 | 5.194931774 |
| 40726_at | KIF11 | 2.94101083 | 0.0093 | 5.1806793 |
| 41400_at | TK1 | 4.245983179 | 0.0093 | 5.167172588 |
| 41409_at | C1orf38 | 3.109232321 | 0.0063 | 5.100239097 |
| 40425_at | EFNA1 | 2.738432716 | 0.0196 | 5.067718102 |
| 32081_at | CIT | 6.162032917 | 0.0027 | 5.043567722 |
| 1108_s_at | EPHA1 | 4.863995126 | 0.0027 | 5.040980858 |
| 33338_at | STAT1 | 3.274771895 | 0.0063 | 5.029498048 |

TABLE 6

Upregulated Genes Expressed At Least 5-Fold Higher In Normal Endometrial Epithelial Cells Compared With Uterine Serous Papillary Carcinoma

| Probe Set | Gene Symbol | SAM Score(d) | p of WRS | Ratio NEC/USPC |
|---|---|---|---|---|
| 774_g_at | MYH11 | 17.6111674 | 0.0027 | 1014.968759 |
| 773_at | MYH11 | 14.26541863 | 0.0027 | 968.0223497 |
| 32582_at | MYH11 | 11.27680376 | 0.0027 | 212.2458648 |
| 36681_at | APOD | 11.7139616 | 0.0027 | 137.3140116 |
| 1501_at | IGF1 | 8.3207956 | 0.0027 | 128.0651104 |
| 39325_at | EBAF | 8.177456434 | 0.0027 | 123.064609 |
| 767_at | — | 12.70747752 | 0.0027 | 119.5409103 |
| 40398_s_at | MEOX2 | 10.18172072 | 0.0027 | 114.9489897 |
| 40776_at | DES | 9.737597758 | 0.0027 | 109.416397 |
| 1197_at | ACTG2 | 5.86136146 | 0.0027 | 96.65715109 |
| 36627_at | SPARCL1 | 7.724402007 | 0.0027 | 93.89302842 |
| 37407_s_at | MYH11 | 11.89270454 | 0.0027 | 88.70362054 |
| 39673_i_at | ECM2 | 8.458527972 | 0.0027 | 82.52353674 |
| 39701_at | PEG3 | 7.644643483 | 0.0027 | 73.87997223 |
| 39066_at | MFAP4 | 9.382764201 | 0.0027 | 68.84723295 |
| 38737_at | IGF1 | 6.340769807 | 0.0027 | 65.13666715 |
| 35730_at | ADH1B | 9.758743372 | 0.0027 | 64.94146631 |
| 41124_r_at | ENPP2 | 7.006678874 | 0.0027 | 53.43118221 |
| 36749_at | CPA3 | 9.095730461 | 0.0027 | 53.07347991 |
| 39616_at | PTGER3 | 10.18818646 | 0.0027 | 52.65326101 |
| 33440_at | TCF8 | 7.220247327 | 0.0027 | 49.54168001 |
| 32666_at | CXCL12 | 7.167916527 | 0.0027 | 49.2359637 |
| 38734_at | PLN | 9.182449981 | 0.0027 | 47.86730799 |
| 34203_at | CNN1 | 5.0508523 | 0.0027 | 47.0209722 |
| 37576_at | PCP4 | 12.46833717 | 0.0027 | 45.45542357 |
| 36834_at | MOXD1 | 9.736431311 | 0.0027 | 44.20917891 |
| 37247_at | TCF21 | 9.809724062 | 0.0027 | 42.40051895 |

TABLE 6-continued

Upregulated Genes Expressed At Least 5-Fold Higher
In Normal Endometrial Epithelial Cells Compared With
Uterine Serous Papillary Carcinoma

| Probe Set | Gene Symbol | SAM Score(d) | p of WRS | Ratio NEC/USPC |
|---|---|---|---|---|
| 37701_at | RGS2 | 7.407533049 | 0.0027 | 42.29038464 |
| 779_at | COL4A6 | 5.840226002 | 0.0027 | 41.96325597 |
| 37394_at | C7 | 9.834950038 | 0.0027 | 40.72326307 |
| 36533_at | PTGIS | 6.097204484 | 0.0027 | 39.10052985 |
| 32689_s_at | — | 6.178363757 | 0.0027 | 36.96897988 |
| 32905_s_at | TPSB2 | 6.87294347 | 0.0027 | 36.85974711 |
| 33240_at | SEMACAP3 | 4.814091817 | 0.0027 | 36.54583796 |
| 1466_s_at | FGF7 | 8.628399247 | 0.0027 | 35.60413415 |
| 32686_at | PTGER3 | 7.396922485 | 0.0027 | 35.31357002 |
| 39690_at | ALP | 6.951347359 | 0.0027 | 33.76045029 |
| 38427_at | COL15A1 | 7.196374501 | 0.0027 | 32.85391153 |
| 39939_at | COL4A6 | 6.846432716 | 0.0027 | 32.53815505 |
| 37630_at | NRLN1 | 5.895556339 | 0.0027 | 31.03030255 |
| 35717_at | ABCA8 | 7.587173679 | 0.0027 | 30.63819827 |
| 1709_g_at | MAPK10 | 6.522200835 | 0.0027 | 30.54331363 |
| 35679_s_at | DPP6 | 5.899443575 | 0.0027 | 30.33959319 |
| 35740_at | EMILIN1 | 7.445413041 | 0.0027 | 29.45261895 |
| 41123_s_at | ENPP2 | 6.597107224 | 0.0027 | 29.29614059 |
| 755_at | ITPR1 | 8.210929741 | 0.0027 | 29.02124207 |
| 32847_at | MYLK | 5.388215885 | 0.0027 | 28.22518538 |
| 38001_at | CACNA1C | 5.739826433 | 0.0027 | 27.31347302 |
| 37279_at | GEM | 9.925280559 | 0.0027 | 26.56613192 |
| 36396_at | — | 5.90098377 | 0.0027 | 26.32457357 |
| 41137_at | PPP1R12B | 12.043235 | 0.0027 | 25.97089935 |
| 41405_at | SFRP4 | 10.07707264 | 0.0027 | 23.90433923 |
| 40775_at | ITM2A | 6.15225431 | 0.0027 | 23.83083993 |
| 38059_g_at | DPT | 6.507962247 | 0.0027 | 23.76376781 |
| 41504_s_at | MAF | 5.331090667 | 0.0027 | 23.65323618 |
| 1596_g_at | TEK | 4.54150328 | 0.0027 | 23.37422615 |
| 914_g_at | ERG | 6.104980572 | 0.0027 | 22.63829292 |
| 34283_at | — | 5.390052481 | 0.0041 | 22.19917455 |
| 34388_at | COL14A1 | 9.452205029 | 0.0027 | 21.48165459 |
| 38994_at | SOCS2 | 6.600175855 | 0.0027 | 21.47663968 |
| 36065_at | LDB2 | 5.790219755 | 0.0027 | 21.19321308 |
| 40230_at | FRZB | 5.962169722 | 0.0027 | 21.00467856 |
| 33790_at | CCL15 | 9.01652793 | 0.0027 | 20.5510028 |
| 33890_at | RGS5 | 7.347159852 | 0.0027 | 20.2203337 |
| 36513_at | MAGP2 | 4.385435702 | 0.0041 | 20.10734871 |
| 32526_at | JAM3 | 6.12916782 | 0.0027 | 19.89641568 |
| 32687_s_at | PTGER3 | 5.902450533 | 0.0027 | 19.7194642 |
| 35638_at | CBFA2T1 | 10.47022487 | 0.0027 | 19.57233853 |
| 34637_f_at | ADH1A | 6.291154915 | 0.0027 | 19.20847669 |
| 34675_at | SBLF | 5.400378777 | 0.0027 | 19.04463285 |
| 38351_at | — | 5.899004809 | 0.0026 | 18.69131208 |
| 1182_at | PLCL1 | 4.047061946 | 0.0027 | 18.50958764 |
| 39681_at | ZNF145 | 6.266146694 | 0.0027 | 18.41823634 |
| 1708_at | MAPK10 | 6.336420306 | 0.0027 | 18.31250756 |
| 37765_at | LMOD1 | 7.585915773 | 0.0027 | 18.11614265 |
| 1678_g_at | IGFBP5 | 4.237261246 | 0.0041 | 17.88349387 |
| 35358_at | TENC1 | 9.24287493 | 0.0027 | 17.68277053 |
| 33442_at | KIAA0367 | 6.829577702 | 0.0027 | 17.58195512 |
| 37249_at | PDE8B | 5.03457122 | 0.0027 | 17.25176904 |
| 33834_at | CXCL12 | 7.735640221 | 0.0027 | 17.10893345 |
| 35324_at | SLIT3 | 5.157473623 | 0.0027 | 17.08441711 |
| 37015_at | ALDH1A1 | 4.941494764 | 0.0027 | 16.83181709 |
| 39266_at | — | 6.23654664 | 0.0027 | 16.80733058 |
| 33462_at | GPR105 | 4.907484265 | 0.0027 | 16.49634139 |
| 32488_at | COL3A1 | 3.927988681 | 0.0027 | 16.44993439 |
| 483_g_at | CDH13 | 3.754937593 | 0.0027 | 16.43857351 |
| 38026_at | FBLN1 | 5.350151734 | 0.0027 | 16.06497318 |
| 1909_at | BCL2 | 7.355936992 | 0.0027 | 16.01160367 |
| 36245_at | HTR2B | 4.697764773 | 0.0027 | 15.77119379 |
| 32057_at | LRRC17 | 5.469946898 | 0.0027 | 15.6891271 |
| 39544_at | DMN | 5.361074255 | 0.0027 | 15.66465434 |
| 37112_at | C6orf32 | 4.719846975 | 0.0027 | 15.65975413 |
| 36733_at | FLJ32389 | 4.441898885 | 0.0027 | 15.64273348 |
| 1319_at | DDR2 | 5.400093727 | 0.0027 | 15.5817123 |
| 38057_at | DPT | 8.478521377 | 0.0027 | 15.51358362 |
| 40358_at | GLI3 | 6.649732557 | 0.0027 | 15.11249492 |
| 38627_at | HLF | 4.946851692 | 0.0027 | 14.89249894 |
| 1731_at | PDGFRA | 7.049550835 | 0.0027 | 14.84422948 |
| 31897_at | DOC1 | 4.66382704 | 0.0027 | 14.80084961 |
| 2073_s_at | CDH13 | 5.076264455 | 0.0027 | 14.79118507 |

TABLE 6-continued

Upregulated Genes Expressed At Least 5-Fold Higher
In Normal Endometrial Epithelial Cells Compared With
Uterine Serous Papillary Carcinoma

| Probe Set | Gene Symbol | SAM Score(d) | p of WRS | Ratio NEC/USPC |
|---|---|---|---|---|
| 38577_at | — | 7.283309694 | 0.0027 | 14.78670234 |
| 38004_at | CSPG4 | 6.071627359 | 0.0027 | 14.40637488 |
| 32109_at | FXYD1 | 7.333234712 | 0.0027 | 14.33463902 |
| 34853_at | FLRT2 | 9.833656085 | 0.0027 | 14.33080432 |
| 38298_at | KCNMB1 | 7.045889128 | 0.0027 | 14.25816751 |
| 41245_at | GDF10 | 6.642690314 | 0.0027 | 14.21467179 |
| 38322_at | GAGEC1 | 6.215440519 | 0.0027 | 14.10508119 |
| 1198_at | EDNRB | 4.898747758 | 0.0027 | 14.08196951 |
| 41505_r_at | MAF | 4.528150651 | 0.0027 | 14.0059518 |
| 36976_at | CDH11 | 3.691860596 | 0.0027 | 14.00329993 |
| 32688_at | PTGER3 | 4.997630756 | 0.0027 | 13.68791213 |
| 1575_at | ABCB1 | 6.210355138 | 0.0027 | 13.64196645 |
| 32778_at | ITPR1 | 4.9135006 | 0.0027 | 13.60359986 |
| 40737_at | KCNMA1 | 5.642312954 | 0.0027 | 13.60011778 |
| 36569_at | TNA | 11.51239349 | 0.0027 | 13.14186685 |
| 1897_at | TGFBR3 | 4.922146191 | 0.0041 | 12.99722509 |
| 2087_s_at | CDH11 | 4.34470878 | 0.0027 | 12.96131894 |
| 34820_at | PTN | 4.413004145 | 0.0041 | 12.94626537 |
| 743_at | NAP1L3 | 7.858619208 | 0.0027 | 12.91061134 |
| 1507_s_at | EDNRA | 4.31923776 | 0.0041 | 12.88466839 |
| 38995_at | CLDN5 | 12.15582555 | 0.0027 | 12.86636376 |
| 1147_at | — | 7.083718066 | 0.0027 | 12.69931721 |
| 1954_at | KDR | 6.076599432 | 0.0027 | 12.6174344 |
| 38786_at | — | 5.676030466 | 0.0027 | 12.61170471 |
| 40757_at | GZMA | 4.574516084 | 0.0041 | 12.56281091 |
| 36695_at | na | 5.77638459 | 0.0027 | 12.53905775 |
| 32052_at | HBB | 5.107109957 | 0.0063 | 12.52262761 |
| 37446_at | GASP | 8.226558005 | 0.0027 | 12.39360585 |
| 38038_at | LUM | 4.46220463 | 0.0027 | 12.34757673 |
| 32889_at | RPIB9 | 6.336650756 | 0.0027 | 12.34540513 |
| 35234_at | RECK | 4.47558162 | 0.0027 | 12.33793353 |
| 661_at | GAS1 | 4.647834984 | 0.0027 | 12.32556384 |
| 41195_at | LPP | 6.291656851 | 0.0027 | 12.26636801 |
| 32664_at | RNASE4 | 6.39454963 | 0.0027 | 11.89680804 |
| 39038_at | FBLN5 | 4.324883809 | 0.0027 | 11.89440528 |
| 40693_at | KCNB1 | 4.95203129 | 0.0041 | 11.84773944 |
| 38052_at | F13A1 | 5.346464847 | 0.0027 | 11.69181717 |
| 35220_at | ENPEP | 4.200434333 | 0.0027 | 11.66308093 |
| 37512_at | RODH | 5.112208975 | 0.0027 | 11.65031202 |
| 103_at | THBS4 | 5.113726559 | 0.0027 | 11.6063075 |
| 36156_at | AQP1 | 6.926726938 | 0.0027 | 11.6016663 |
| 39593_at | FGL2 | 5.175765324 | 0.0027 | 11.38223584 |
| 33248_at | HOXA11 | 6.555467127 | 0.0027 | 11.34828098 |
| 41420_at | IGFBP5 | 4.165576966 | 0.0041 | 11.32365037 |
| 35644_at | HEPH | 6.666296008 | 0.0027 | 11.26324425 |
| 39646_at | CACNB2 | 4.718873234 | 0.0027 | 11.25017414 |
| 35333_r_at | DVS27 | 4.403332874 | 0.0027 | 11.23759398 |
| 33182_at | — | 4.990249409 | 0.0027 | 11.20258783 |
| 34303_at | FLJ90798 | 4.908581714 | 0.0027 | 11.10458088 |
| 33756_at | AOC3 | 5.185884024 | 0.0027 | 11.09776026 |
| 37710_at | MEF2C | 7.484609789 | 0.0027 | 11.03832245 |
| 35680_r_at | DPP6 | 3.78344404 | 0.0027 | 10.88151987 |
| 40126_at | — | 4.62026524 | 0.0027 | 10.87424764 |
| 31831_at | SMTN | 5.711671156 | 0.0027 | 10.84917408 |
| 234_s_at | PTN | 5.660081325 | 0.0041 | 10.803161 |
| 36939_at | GPM6A | 4.980509075 | 0.0027 | 10.76644676 |
| 41158_at | PLP1 | 4.878943567 | 0.0027 | 10.76462278 |
| 41839_at | GAS1 | 4.40075134 | 0.0027 | 10.75375673 |
| 1186_at | GDF10 | 4.165439023 | 0.0063 | 10.74677086 |
| 35404_at | TACR2 | 4.416070077 | 0.0063 | 10.67366905 |
| 160023_at | WNT2 | 5.423667844 | 0.0027 | 10.67077677 |
| 34561_at | MS4A2 | 6.379719275 | 0.0027 | 10.6336763 |
| 36280_at | GZMK | 4.739332721 | 0.0027 | 10.5607572 |
| 35668_at | RAMP1 | 3.430294187 | 0.0027 | 10.4886967 |
| 32521_at | SFRP1 | 4.488454671 | 0.0027 | 10.43051698 |
| 1975_s_at | IGF1 | 7.381010481 | 0.0027 | 10.34307322 |
| 37671_at | LAMA4 | 5.094401298 | 0.0027 | 10.34084543 |
| 40013_at | CLIC2 | 5.388103426 | 0.0027 | 10.2736905 |
| 32782_r_at | BPAG1 | 4.596569018 | 0.0027 | 10.2197061 |
| 36918_at | GUCY1A3 | 4.344175119 | 0.0027 | 10.18606373 |
| 32239_at | MATN2 | 6.196807922 | 0.0027 | 10.14895891 |
| 36503_at | CCL21 | 6.812268911 | 0.0027 | 10.09354903 |
| 38508_s_at | TNXB | 8.826474643 | 0.0027 | 10.0794719 |

TABLE 6-continued

Upregulated Genes Expressed At Least 5-Fold Higher In Normal Endometrial Epithelial Cells Compared With Uterine Serous Papillary Carcinoma

| Probe Set | Gene Symbol | SAM Score(d) | p of WRS | Ratio NEC/USPC |
|---|---|---|---|---|
| 35146_at | TGFB1I1 | 5.5617525 | 0.0027 | 10.0680837 |
| 38653_at | PMP22 | 6.084746373 | 0.0027 | 10.04665889 |
| 342_at | ENPP1 | 5.008283422 | 0.0041 | 10.0434301 |
| 32826_at | ENTPD1 | 6.422625578 | 0.0027 | 10.01186286 |
| 40318_at | DNCI1 | 3.347919999 | 0.0063 | 10.00454416 |
| 32781_f_at | BPAG1 | 3.895818151 | 0.0027 | 9.99877625 |
| 40202_at | BTEB1 | 5.752005719 | 0.0027 | 9.966240854 |
| 40856_at | SERPINF1 | 6.638116781 | 0.0027 | 9.959239422 |
| 40560_at | TBX2 | 6.427628478 | 0.0027 | 9.957108857 |
| 33355_at | PBX1 | 6.203118598 | 0.0027 | 9.938502929 |
| 39945_at | FAP | 3.442260355 | 0.0041 | 9.899321818 |
| 41549_s_at | AP1S2 | 6.153046901 | 0.0027 | 9.800866773 |
| 34760_at | DCL-1 | 4.968676715 | 0.0027 | 9.737016618 |
| 34990_at | SETBP1 | 4.786102171 | 0.0027 | 9.73531319 |
| 35459_at | RGS13 | 4.318971444 | 0.0063 | 9.73086055 |
| 37716_at | MOX2 | 6.058611716 | 0.0027 | 9.730316399 |
| 40301_at | RE2 | 4.30887411 | 0.0027 | 9.580304305 |
| 35742_at | BC008967 | 4.439963322 | 0.0027 | 9.57255333 |
| 39674_r_at | ECM2 | 6.458114792 | 0.0027 | 9.556122049 |
| 36993_at | PDGFRB | 4.280198113 | 0.0027 | 9.498903399 |
| 37919_at | SLC21A2 | 5.026176297 | 0.0041 | 9.412820802 |
| 38837_at | DJ971N18.2 | 6.539256063 | 0.0027 | 9.396781505 |
| 36442_g_at | KCNMA1 | 5.555835457 | 0.0027 | 9.394855646 |
| 38177_at | RAMP2 | 5.549671233 | 0.0027 | 9.393838874 |
| 36894_at | CBX7 | 8.966175904 | 0.0027 | 9.37016198 |
| 40646_at | CX3CR1 | 5.239286889 | 0.0027 | 9.327761215 |
| 32143_at | OSR2 | 5.813502921 | 0.0027 | 9.305772959 |
| 35366_at | NID | 3.807200874 | 0.0027 | 9.274271385 |
| 32667_at | COL4A5 | 4.185428011 | 0.0027 | 9.271586005 |
| 32780_at | BPAG1 | 5.55884169 | 0.0027 | 9.258012771 |
| 36042_at | NTRK2 | 5.561146153 | 0.0027 | 9.250870262 |
| 33295_at | FY | 7.084139876 | 0.0027 | 9.106257274 |
| 38228_g_at | MITF | 6.102946294 | 0.0027 | 9.105582903 |
| 36073_at | NDN | 3.559985604 | 0.0027 | 9.063290854 |
| 39750_at | — | 8.467774719 | 0.0027 | 9.019572879 |
| 39771_at | RHOBTB1 | 4.574178485 | 0.0027 | 8.990229715 |
| 607_s_at | VWF | 5.356332342 | 0.0027 | 8.958228604 |
| 1577_at | AR | 3.825402089 | 0.0041 | 8.912555487 |
| 33303_at | SSPN | 4.096449745 | 0.0027 | 8.868579212 |
| 38028_at | DAT1 | 4.626935347 | 0.0027 | 8.86276571 |
| 37983_at | AGTR1 | 6.183093963 | 0.0027 | 8.827871738 |
| 40046_r_at | C18orf1 | 5.605179701 | 0.0027 | 8.779676657 |
| 1767_s_at | TGFB3 | 7.525905116 | 0.0027 | 8.765570787 |
| 39714_at | SH3BGRL | 4.93580005 | 0.0027 | 8.76401131 |
| 36606_at | CPE | 4.727031789 | 0.0027 | 8.748823414 |
| 38120_at | PKD2 | 6.187924359 | 0.0027 | 8.723317835 |
| 36867_at | — | 5.502645605 | 0.0027 | 8.681195794 |
| 38113_at | SYNE1 | 4.961267087 | 0.0027 | 8.667220225 |
| 33733_at | ABCG2 | 5.755109102 | 0.0027 | 8.636931554 |
| 35681_r_at | ZFHX1B | 3.362927284 | 0.0027 | 8.619823363 |
| 39317_at | — | 4.725601909 | 0.0027 | 8.587430684 |
| 1500_at | WT1 | 4.331555572 | 0.0041 | 8.574447585 |
| 40017_at | DKFZP586H2123 | 3.36169877 | 0.0027 | 8.559319409 |
| 1625_at | — | 5.121462166 | 0.0027 | 8.490942275 |
| 129_g_at | CTSK | 4.3842531 | 0.0027 | 8.419453396 |
| 41784_at | DKFZp564B0769 | 4.61026234 | 0.0027 | 8.419008886 |
| 41290_at | — | 3.544096357 | 0.0093 | 8.400345338 |
| 1591_s_at | IGF2 | 3.561710606 | 0.0041 | 8.324420931 |
| 36021_at | LEF1 | 4.051827392 | 0.0027 | 8.238834587 |
| 1771_s_at | PDGFRB | 3.650542935 | 0.0027 | 8.225807768 |
| 38466_at | CTSK | 3.787589001 | 0.0041 | 8.197720493 |
| 1380_at | FGF7 | 5.524953025 | 0.0027 | 8.121593377 |
| 41013_at | FLJ31737 | 6.592336358 | 0.0027 | 8.107620424 |
| 859_at | CYP1B1 | 3.751490096 | 0.0063 | 8.082690646 |
| 31902_at | DIO2 | 4.316229908 | 0.0027 | 8.06806751 |
| 34995_at | CALCRL | 5.70953518 | 0.0027 | 8.052189461 |
| 32126_at | FGF7 | 4.234501237 | 0.0027 | 8.042021298 |
| 37398_at | PECAM1 | 4.329117802 | 0.0027 | 8.016895704 |
| 38042_at | G6PD | 6.987010631 | 0.0027 | 8.016883235 |
| 32779_s_at | ITPR1 | 6.416481452 | 0.0027 | 7.974320137 |
| 32542_at | FHL1 | 4.425372331 | 0.0027 | 7.941951703 |
| 39031_at | COX7A1 | 3.414853092 | 0.0027 | 7.901991161 |
| 37863_at | EGR2 | 3.653408914 | 0.0027 | 7.862848151 |

TABLE 6-continued

Upregulated Genes Expressed At Least 5-Fold Higher In Normal Endometrial Epithelial Cells Compared With Uterine Serous Papillary Carcinoma

| Probe Set | Gene Symbol | SAM Score(d) | p of WRS | Ratio NEC/USPC |
|---|---|---|---|---|
| 40475_at | CAPN6 | 4.123958511 | 0.0027 | 7.840245281 |
| 36882_at | HOXD9 | 4.651878446 | 0.0027 | 7.823908297 |
| 38174_at | PSD | 6.229841181 | 0.0027 | 7.816130898 |
| 33431_at | FMOD | 4.128438324 | 0.0027 | 7.815908163 |
| 40841_at | TACC1 | 6.85110732 | 0.0027 | 7.795011222 |
| 33817_at | HNRPA3 | 6.302017315 | 0.0027 | 7.787750832 |
| 40913_at | ATP2B4 | 3.846256488 | 0.0027 | 7.776240242 |
| 1396_at | — | 3.120644286 | 0.0063 | 7.748987482 |
| 38288_at | SNAI2 | 4.162425417 | 0.0041 | 7.728278549 |
| 38312_at | LOC169611 | 5.745797039 | 0.0027 | 7.703588116 |
| 38650_at | — | 2.889673044 | 0.0027 | 7.644382939 |
| 37598_at | RASSF2 | 3.481277121 | 0.0093 | 7.576353353 |
| 40698_at | CLECSF2 | 4.080958193 | 0.0027 | 7.516722321 |
| 36917_at | LAMA2 | 4.758295806 | 0.0027 | 7.50983691 |
| 38875_r_at | GREB1 | 3.932392202 | 0.0041 | 7.503944317 |
| 128_at | CTSK | 3.912325952 | 0.0027 | 7.490867771 |
| 39063_at | ACTC | 3.50984153 | 0.0136 | 7.462854816 |
| 36311_at | PDE1A | 4.408892423 | 0.0027 | 7.400144084 |
| 38181_at | MMP11 | 3.440836069 | 0.0136 | 7.215260166 |
| 414_at | HOXD10 | 4.48610318 | 0.0027 | 7.165970315 |
| 37560_at | FLJ00133 | 4.618261212 | 0.0027 | 7.113754721 |
| 41388_at | MEIS2 | 5.209442647 | 0.0027 | 7.102590023 |
| 40716_at | — | 5.682826784 | 0.0027 | 7.087402622 |
| 41837_at | — | 3.749728537 | 0.0063 | 7.086919982 |
| 33239_at | MGC33887 | 3.781769332 | 0.0027 | 7.064070455 |
| 35678_at | PCDH7 | 4.599768253 | 0.0027 | 7.055958628 |
| 41287_s_at | CALM1 | 4.9159385 | 0.0027 | 6.980202617 |
| 32119_at | — | 4.11125462 | 0.0027 | 6.969578438 |
| 36908_at | MRC1 | 3.916253996 | 0.0027 | 6.960776505 |
| 38636_at | ISLR | 6.658140679 | 0.0027 | 6.952656256 |
| 40071_at | CYP1B1 | 3.542253289 | 0.0063 | 6.931496169 |
| 36149_at | DPYSL3 | 4.256411985 | 0.0041 | 6.92915584 |
| 37205_at | FBXL7 | 3.820866964 | 0.0027 | 6.919005089 |
| 268_at | — | 3.904361484 | 0.0027 | 6.915726506 |
| 32728_at | AMPH | 4.439623421 | 0.0027 | 6.837387527 |
| 36577_at | PLEKHC1 | 4.82253418 | 0.0027 | 6.829191126 |
| 38315_at | ALDH1A2 | 5.390933518 | 0.0027 | 6.759589253 |
| 41536_at | ID4 | 3.893377567 | 0.0027 | 6.742578708 |
| 38420_at | COL5A2 | 3.546028887 | 0.0041 | 6.703606937 |
| 39647_s_at | CACNB2 | 6.114983417 | 0.0027 | 6.669834349 |
| 36505_at | CASQ2 | 4.034975973 | 0.0027 | 6.608279434 |
| 32570_at | HPGD | 4.182995735 | 0.0027 | 6.596383607 |
| 31790_at | STARD13 | 4.986919151 | 0.0041 | 6.580417745 |
| 40767_at | TFPI | 5.047863935 | 0.0027 | 6.564786304 |
| 1535_at | CHES1 | 4.241079307 | 0.0027 | 6.553244809 |
| 32182_at | STK38L | 4.706516629 | 0.0041 | 6.543532522 |
| 40191_s_at | KIAA0582 | 4.468954313 | 0.0027 | 6.537990728 |
| 34377_at | ATP1A2 | 4.345740288 | 0.0027 | 6.442188895 |
| 36534_at | KIAA1735 | 5.605691943 | 0.0027 | 6.434650624 |
| 34257_at | AIP1 | 5.597880058 | 0.0027 | 6.413861576 |
| 38317_at | TCEAL1 | 5.544448535 | 0.0027 | 6.400529452 |
| 38669_at | SLK | 4.4731488 | 0.0027 | 6.395945769 |
| 33910_at | PTPRD | 3.451476556 | 0.0063 | 6.326797395 |
| 38407_r_at | PTGDS | 3.508676618 | 0.0041 | 6.2537194 |
| 36521_at | DZIP1 | 3.333044376 | 0.0027 | 6.229375084 |
| 35622_at | SLI | 3.925359668 | 0.0063 | 6.225537025 |
| 40328_at | TWIST1 | 3.703806272 | 0.0063 | 6.213773777 |
| 41448_at | HOXA10 | 5.498866772 | 0.0027 | 6.207688396 |
| 36096_at | FLJ13110 | 5.000819145 | 0.0027 | 6.193515832 |
| 38408_at | TM4SF2 | 3.772993241 | 0.0063 | 6.181162174 |
| 41412_at | PIPPIN | 4.595014514 | 0.0041 | 6.179362052 |
| 35645_at | SNX1 | 6.206010457 | 0.0027 | 6.139850996 |
| 1601_s_at | — | 3.506288374 | 0.0093 | 6.131115111 |
| 40488_at | DMD | 4.488235032 | 0.0027 | 6.086194006 |
| 482_at | CDH13 | 3.85482903 | 0.0027 | 6.078949974 |
| 31855_at | SRPX | 4.594388673 | 0.0027 | 6.061823385 |
| 41796_at | PLCL2 | 4.149979666 | 0.0041 | 6.060598274 |
| 719_g_at | PRSS11 | 3.302739151 | 0.0027 | 6.021056622 |
| 696_at | — | 3.545443995 | 0.0041 | 6.01634733 |
| 34216_at | KLF7 | 3.766915537 | 0.0063 | 5.957634877 |
| 35692_at | RIS1 | 3.353524837 | 0.0027 | 5.920347327 |
| 36258_at | PRKG1 | 3.430746034 | 0.0027 | 5.886138767 |
| 39069_at | AEBP1 | 2.937772018 | 0.0027 | 5.878905586 |

TABLE 6-continued

Upregulated Genes Expressed At Least 5-Fold Higher
In Normal Endometrial Epithelial Cells Compared With
Uterine Serous Papillary Carcinoma

| Probe Set | Gene Symbol | SAM Score(d) | p of WRS | Ratio NEC/USPC |
|---|---|---|---|---|
| 40839_at | UBL3 | 4.622359971 | 0.0041 | 5.876076773 |
| 31982_at | SORBS1 | 3.386365547 | 0.0041 | 5.845348994 |
| 34235_at | GPR116 | 4.838344706 | 0.0041 | 5.836924195 |
| 39397_at | NR2F2 | 6.424176938 | 0.0027 | 5.818493808 |
| 40075_at | SYT1 | 4.767353132 | 0.0041 | 5.776146594 |
| 37543_at | ARHGEF6 | 6.674769949 | 0.0027 | 5.771235708 |
| 33387_at | GAS7 | 3.527723529 | 0.0041 | 5.758434115 |
| 34015_at | PTGFR | 3.205361762 | 0.0136 | 5.742603773 |
| 39950_at | ASM3A | 5.096868564 | 0.0027 | 5.741120565 |
| 36095_at | CLIPR-59 | 3.524586182 | 0.0027 | 5.736208783 |
| 34797_at | PPAP2A | 6.402521028 | 0.0027 | 5.705386452 |
| 40763_at | MEIS1 | 3.790421308 | 0.0027 | 5.6975795 |
| 35948_at | ITGA9 | 4.89260679 | 0.0041 | 5.693603423 |
| 34023_at | FCER1A | 3.259096027 | 0.0041 | 5.685370893 |
| 37051_at | KCNN3 | 4.327976299 | 0.0027 | 5.681982346 |
| 37628_at | MAOB | 3.961145375 | 0.0093 | 5.659562947 |
| 41478_at | — | 4.097311966 | 0.0027 | 5.656302505 |
| 1467_at | EPS8 | 4.546724195 | 0.0041 | 5.647160627 |
| 32527_at | APM2 | 3.04326955 | 0.0136 | 5.646392299 |
| 40576_f_at | HNRPDL | 5.544877803 | 0.0027 | 5.641607337 |
| 38748_at | ADARB1 | 4.239414077 | 0.0027 | 5.630091556 |
| 32307_s_at | COL1A2 | 3.077946747 | 0.0027 | 5.610938857 |
| 37604_at | HNMT | 4.685376668 | 0.0027 | 5.60567914 |
| 41739_s_at | CALD1 | 3.835849971 | 0.0027 | 5.566506265 |
| 31830_s_at | SMTN | 5.187606432 | 0.0027 | 5.536338862 |
| 1958_at | FIGF | 3.87790423 | 0.0027 | 5.530479685 |
| 37842_at | HIC | 5.230871247 | 0.0027 | 5.520045776 |
| 37600_at | ECM1 | 3.271948767 | 0.0027 | 5.51149006 |
| 40448_at | ZFP36 | 5.469746743 | 0.0027 | 5.505331184 |
| 36061_at | SEMA5A | 5.299762537 | 0.0027 | 5.499436404 |
| 34192_at | COH1 | 4.663835693 | 0.0027 | 5.498908277 |
| 659_g_at | THBS2 | 3.250443928 | 0.0093 | 5.488143801 |
| 32851_at | CUGBP2 | 4.172100946 | 0.0027 | 5.480623377 |
| 34802_at | COL6A2 | 3.774964096 | 0.0027 | 5.472446424 |
| 481_at | SNRK | 2.494696971 | 0.0196 | 5.44491364 |
| 41378_at | SGCD | 3.588550024 | 0.0041 | 5.435392672 |
| 32740_at | Rab11-FIP2 | 3.54373784 | 0.0041 | 5.429822613 |
| 41028_at | RYR3 | 4.132282077 | 0.0027 | 5.384932561 |
| 39123_s_at | TRPC1 | 3.623665783 | 0.0027 | 5.327776817 |
| 37841_at | BCHE | 4.581864247 | 0.0027 | 5.32221997 |
| 2094_s_at | FOS | 3.072963845 | 0.0136 | 5.314613874 |
| 37366_at | LIM | 6.021012841 | 0.0027 | 5.314441359 |
| 160029_at | PRKCB1 | 4.108606566 | 0.0063 | 5.294770685 |
| 615_s_at | PTHLH | 3.120886497 | 0.0136 | 5.278419862 |
| 718_at | PRSS11 | 3.543714365 | 0.0027 | 5.257009628 |
| 38227_at | MITF | 5.771493332 | 0.0027 | 5.251250656 |
| 40199_at | MSX1 | 3.266467021 | 0.0027 | 5.232971855 |
| 1529_at | 13CDNA73 | 4.977414815 | 0.0027 | 5.214598483 |
| 32371_at | KIAA0527 | 3.324238194 | 0.0027 | 5.208457414 |
| 38957_at | DCAMKL1 | 3.228540429 | 0.0093 | 5.205512163 |
| 40746_at | GRIA2 | 2.97000806 | 0.0027 | 5.181047723 |
| 33658_at | ZNF124 | 3.0703345 | 0.0027 | 5.158102761 |
| 41859_at | UST | 4.126895577 | 0.0093 | 5.151465368 |
| 38126_at | BGN | 4.006564606 | 0.0027 | 5.14050562 |
| 38220_at | DPYD | 2.983416919 | 0.0063 | 5.139610847 |
| 38294_at | HOXD4 | 4.823268726 | 0.0041 | 5.138269153 |
| 37225_at | KANK | 5.494612189 | 0.0027 | 5.134298593 |
| 36089_at | INPP5F | 5.042825581 | 0.0027 | 5.133241496 |
| 31823_at | CUTL1 | 5.021790489 | 0.0041 | 5.11768676 |
| 36448_at | — | 3.890991953 | 0.0027 | 5.110789001 |
| 34417_at | FLJ36166 | 5.812546119 | 0.0027 | 5.106099227 |
| 31687_f_at | HBB | 3.813508725 | 0.0136 | 5.092799127 |
| 38717_at | DKFZP586A0522 | 2.964163964 | 0.0063 | 5.085371203 |
| 1970_s_at | FGFR2 | 2.814367366 | 0.0136 | 5.080491239 |
| 32769_at | WDFY3 | 4.794833664 | 0.0027 | 5.064409438 |
| 41031_at | OMD | 3.179437346 | 0.0093 | 5.049649007 |
| 38430_at | FABP4 | 3.825907049 | 0.0041 | 5.045289037 |
| 735_s_at | — | 4.840928699 | 0.0027 | 5.035949376 |
| 36707_s_at | CDKL5 | 4.404644205 | 0.0041 | 5.032600633 |
| 32313_at | TPM2 | 3.296609047 | 0.0041 | 5.010974485 |
| 40570_at | FOXO1A | 4.524987938 | 0.0027 | 5.007343169 |

Example 9

Validation of Microarray Data

Quantitative real-time PCR assays as described above were used to validate the microarray data. Seven highly differentially expressed genes between uterine serous papillary carcinoma and normal endometrial epithelial cells (i.e., CDKN2A/p16, CDKN2A/p14ARF, L1CAM, claudin 3, claudin 4, GRB-7 and c-erbB2) were selected for the analysis.

Primers for L1CAM, claudin-3, and claudin-4 were obtained from Applied Biosystems as assay on demand products. Assays ID were Hs00170849_ml (L1CAM), Hs00265816_s1 (claudin-3), and Hs00533616_s1 (claudin-4). GRB7 primers sequences were: forward, 5'-TCTACGG-GATGACCACTGA-3' (SEQ ID NO.1); reverse, 5'-CGAAGCCCCTTGTGTCCA-3' (SEQ ID NO.2). c-erbB2 primers sequences were: forward, 5'-GTATACAT-TCGGCGCCAGCT-3' (SEQ ID NO.3); reverse, 5'-GCA-GACGAGGGTGCAGGA-3' (SEQ ID NO.4). CDKN2A/p16 primers sequences were: forward, 5'-CCCAAACGCAC-CGAATAGTTAC-3' (SEQ ID NO.5); reverse, 5'-ATTC-CAATTCCCCTGCAAACT-3' (SEQ ID NO.6). CDKN2A/p14ARF primers sequences were: forward, 5'-TGATGCTACTGAGGAGCCAGC-3' (SEQ ID NO.7); reverse, 5'-AGGGCCTTTCCTACCTGGTC-3' (SEQ ID NO.8). Amplification was carried out by using 1 unit of polymerase in a final volume of 20 µl containing 2.5 mM $MgCl_2$. TaqGold was activated by incubation at 96° C. for 12 min, and the reactions were cycled 26-30 times at 95° C. for 1 min, 55° C. for 1 min, and 72° C. for 1 min, followed by a final extension at 72° C. for 10 min. PCR products were visualized on 2% agarose gels stained with ethidium bromide, and images were captured by an Ultraviolet Products Image Analysis System. Differences between the tumor and normal cells were tested using the Kruskal-Wallis nonparametric test. Pearson product-moment correlations were used to estimate the degree of association between the microarray and quantitative real-time PCR data.

Figure 7:
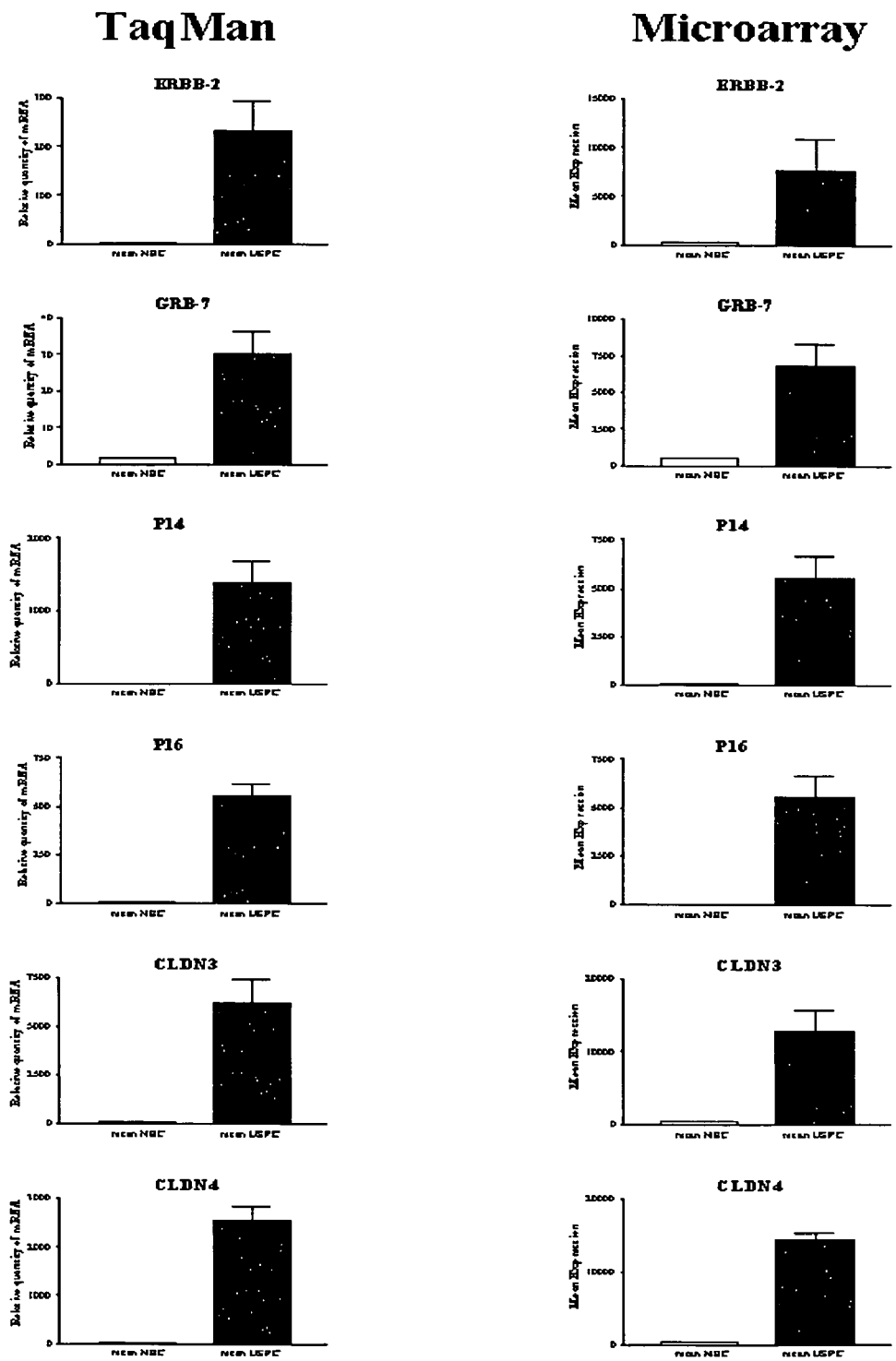
FIG. 7 shows quantitative real-time PCR and microarray expression analysis of CDKN2A/p16, CDKN2A/p14ARF, L1CAM, claudin 3, claudin 4, GRB-7 and c-erbB2 genes differentially expressed between uterine serous papillary carcinoma and normal endometrial epithelial cells.

As shown in FIG. 7, expression differences between uterine serous papillary carcinoma and normal endometrial epithelial cells for CDKN2A/p16 (p=0.002), CDKN2A/p14ARF (p=0.002), L1CAM (p=0.01), claudin 3 (p=0.01), claudin-4 (p=0.002), GRB-7 (p=0.002) and c-erbB2 (p=0.01) were readily apparent. Moreover, for all seven genes tested, the quantitative real-time PCR data were highly correlated to the microarray data (p<0.001) (r=0.81, 0.80, 0.75, 0.69, 0.82, 0.71 and 0.65, respectively). Thus, the PCR data suggest that most array probe sets are likely to accurately measure the levels of the intended transcript within a complex mixture of transcripts.

Example 10

Immunohistochemical Analysis of Claudin-4 Expression

An important issue is whether differences in gene expression result in meaningful differences in protein expression. A second crucial issue is whether gene expression in short term in vitro culture of primary tumor and normal cells may be comparable to uncultured cells from which the primary cell lines were derived. Claudin-4 protein expression was thus evaluated by immunohistochemical staining on formalin-fixed tumor tissue from which primary cultures were obtained. In addition, to further confirm transcriptional profiling results of uterine serous papillary carcinoma, claudin-4 marker was also evaluated by immunohistochemistry in a second independent set of 10 uterine serous papillary carcinoma clinical tissue samples obtained from patients harboring advanced stage disease (i.e., stage III and IV).

Study blocks were selected after histopathologic review by a surgical pathologist. The most representative hematoxylin and eosin-stained block sections were used for each specimen. Briefly, immunohistochemical stains were performed on 4 mm-thick sections of formalin-fixed, paraffin embedded tissue. After pretreatment with 10 mM citrate buffer at pH 6.0 using a steamer, the samples were incubated with mouse anti-claudin-4 antibodies (Zymed Laboratories Inc. San Francisco, Calif.) at 1:2000 dilution. Antigen-bound primary antibodies were detected using standard avidin-biotin immunoperoxidase complex (Dako Corp., Carpinteria, Calif.). Cases with less than 10% staining in tumor cells were considered negative for claudin expression, whereas positive cases were classified as follows regarding the intensity of claudin-4 protein expression: +, medium to weak staining; and ++, medium to intense staining. Subcellular localization (membrane or cytoplasm) was also noted.

Figure 8A:
FIG. 8 shows representative immunohistochemical staining for claudin-4 of 2 paraffin-embedded uterine serous papillary carcinoma (USPC) and 1 normal endometrial epithelial cell (NEC) specimens. NEC 1 (upper panel) showed light membrane staining for claudin-4 while USPC 1 and USPC 3 showed heavy cytoplasmic and membranous staining for claudin-4 (middle and lower panel). Original magnification 400×.
Figure 8B:
Figure 8C:
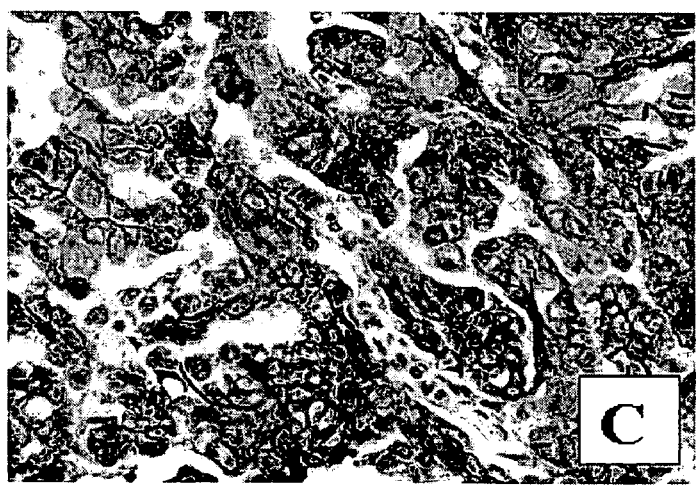

FIG. 8 shows immunohistochemical staining on formalin-fixed tumor tissue from which primary cultures were obtained. Heavy cytoplasmic and membranous staining for claudin-4 protein expression wee noted in all uterine serous papillary carcinoma specimens that overexpressed the claudin-4 gene. In contrast, only low membranous staining for claudin-4 protein was found in normal endometrial epithelial tissue samples.

To confirm and validate the immunohistochemical result data in an independent series of tumor and normal tissues, formalin-fixed tumor tissue blocks from another 13 surgical specimens (i.e., 10 uterine serous papillary carcinoma obtained from patients harboring advanced stage disease and 3 age-matched normal endometrial epithelial cells samples) were tested for claudin-4 expression. Again, in agreement with microarray data, moderate to heavy cytoplasmic and membranous staining for the claudin-4 receptor was found in 100% of the uterine serous papillary carcinoma tested (i.e., 90% score++ and 10% score+) while NEC showed light membranous staining in only 40% of the samples (p=0.02, uterine serous papillary carcinoma vs normal endometrial epithelial cells by student t test).

The following references were cited herein:

Bongso et al., *Human Reproduction* 3:705-13 (1988).
Eisen et al., *Proc Natl Aca Sci USA* 95:14863-68 (1998).
Ismail et al., *Cancer Res.* 60:6744-6749 (2000).
Meresman et al., *Fertility & Sterility* 80 Suppl 2:702-7 (2003).
Santin et al., *Am. J. Obstet. Gynecol.* 183: 601-609 (2000).
Santin et al., *Brit. J. Cancer* 86:151-157 (2002).
Tusher et al., *Proc Natl Acad Sci USA* 98:5116-5121 (2001).
Zhan et al., *Blood* 99:1745-57 (2002).

What is claimed is:

1. A method of detecting uterine serous papillary carcinoma in a human individual, comprising the steps of:

examining gene expression levels of a group of genes comprising ERBB2, PROML1, SFRP1, STC1, F2R, MEN1, TAC1, SLC1A1, KIAA0918, AF038169, HRASLS3, UGT2B7, PTGER2, GRB7, INHBB, SLC6A12, MUC4, CSPG5, PDZK1, RLN2, PKIA, QPRT, PTPRM, PSPHL, PTPRM, AKAP2, RAGD, KIAA1157, PADI2, CCNE1, GGT2, PAX8, GPC4, MYO7A, TJP3, UCHL1, INPP4B, PLAGL1, TMEFF1, IDI1, NEU1, DMD, TUBB, SDC2, ZNF91, INA, TP53BP2, ELKS, FLJ13612, DKFZP566A1524, SLC25A1, ACO1, LOC51760, BNIP3L, CDH1, HIVEP2, API5, NEK2, ARSDR1, CPO, PRRG1, PAX8, PIK3C2B, KIAA0790, CDKN2A, KRTHB1, SAA1, KRT7, TFAP2A, MAP17, LCN2, EEF1A2, L1CAM, VGLL1, GAL, KLK10, IL6, MAL, PI3, PTTG1, WNT7A, CST6, CDC20, KRTHA4, KLK6, CCNE1, KIF2C, KIBRA, UBE2C, CLDN4, DKK1, TNNT1, BIK, CRABP1, STK6, NMU, TPX2, HIST1H1C, IL18, TNNI3, TTK, MICB, SPOCK2, SLC7A5, KRT18, BF, PDXK, RAI3, LAMP3, HMGA1, WNT7A, LAMB3, CENPA, BUB1, ITGA3, CCNE1, CLDN3, RAI3, CCNB1, ANXA2, TK1, FOXM1, TNIP1, CCNB2, F2RL1, TGFA, CCNB1, ANXA3, ITPR3, CDA, EPHB2, PRSS8, PLAUR, FOXD1, CA2, AD024, SPINT2, WFDC2, LAMC2, KIFC1, TRIM16, CDC6, CLDN7, CCNA2, TM4SF11, ESPL1, GALNT3, IL8, KIAA0746, B3GNT3, G1P2, SCNN1A, HMMR, TNFAIP2, TRIP13, PMAIP1, ETV4, MAPK13, CKS1B, NFE2L3, TOP2A, EXO1, SLC16A3, PLK, MYBL2, KPNA2, LAD1, TOP2A, IRAK1, GALE, ITGB8, IMP-3, VAMP8, SERPINB8, INA, BUB1B, ERBB3, SLPI, E2-EPF, FEN1, PPFIA1, KIF11, TK1, C1orf38, EFNA1, CIT, EPHA1, and STAT1 in a uterine sample from the human; and performing statistical analysis on the expression levels of said genes in the uterine sample as compared to expression levels thereof in ovarian tumor samples from individuals with ovarian serous papillary carcinoma, wherein overexpression of said genes compared to expression levels thereof in the individuals with ovarian serous papillary carcinoma, indicates that said individual has uterine serous papillary carcinoma.

2. The method of claim 1, wherein said gene expression is examined by DNA microarray.

3. The method of claim 1, wherein said gene expression is examined at the RNA level.

4. The method of claim 1, wherein said statistical analysis is hierarchical cluster analysis.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<221> NAME/KEY: primer_bind
<223> OTHER INFORMATION: forward primer for GRB7

<400> SEQUENCE: 1
tctacgggat gaccactga                                                                 19

<210> SEQ ID NO 2
<211> LENGTH: 18
<212> TYPE: DNA
<213> ORGANISM: Artificial Sequence
<220> FEATURE:
<221> NAME/KEY: primer_bind
<223> OTHER INFORMATION: reverse primer for GRB7

<400> SEQUENCE: 2
cgaagcccct tgtgtcca                                                                  18

<210> SEQ ID NO 3
<211> LENGTH: 20
<212> TYPE: DNA
<213> ORGANISM: Artificial Sequence
<220> FEATURE:
<221> NAME/KEY: primer_bind
<223> OTHER INFORMATION: forward primer for c-erbB2

<400> SEQUENCE: 3
gtatacattc ggcgccagct                                                                20

<210> SEQ ID NO 4
<211> LENGTH: 18
<212> TYPE: DNA
<213> ORGANISM: Artificial Sequence
<220> FEATURE:
<221> NAME/KEY: primer_bind
<223> OTHER INFORMATION: reverse primer for c-erbB2

<400> SEQUENCE: 4
gcagacgagg gtgcagga                                                                  18

<210> SEQ ID NO 5
<211> LENGTH: 22
<212> TYPE: DNA
<213> ORGANISM: Artificial Sequence
<220> FEATURE:
<221> NAME/KEY: primer_bind
<223> OTHER INFORMATION: forward primer for CDKN2A/p16

<400> SEQUENCE: 5
cccaaacgca ccgaatagtt ac                                                             22

<210> SEQ ID NO 6
<211> LENGTH: 21
<212> TYPE: DNA
<213> ORGANISM: Artificial Sequence
<220> FEATURE:
<221> NAME/KEY: primer_bind
<223> OTHER INFORMATION: reverse primer for CDKN2A/p16

<400> SEQUENCE: 6

```
attccaattc ccctgcaaac t                                            21

<210> SEQ ID NO 7
<211> LENGTH: 21
<212> TYPE: DNA
<213> ORGANISM: Artificial Sequence
<220> FEATURE:
<221> NAME/KEY: primer_bind
<223> OTHER INFORMATION: forward primer for CDKN2A/p14ARF

<400> SEQUENCE: 7
tgatgctact gaggagccag c                                            21

<210> SEQ ID NO 8
<211> LENGTH: 20
<212> TYPE: DNA
<213> ORGANISM: Artificial Sequence
<220> FEATURE:
<221> NAME/KEY: primer_bind
<223> OTHER INFORMATION: reverse primer for CDKN2A/p14ARF

<400> SEQUENCE: 8
agggcctttc ctacctggtc                                              20

<210> SEQ ID NO 9
<211> LENGTH: 1222
<212> TYPE: DNA
<213> ORGANISM: Homosapiens
<220> FEATURE:
<223> OTHER INFORMATION: sequence for AF038169

<400> SEQUENCE: 9
gcttttagag cactgtgatg taacatgtca agcagaaata gggagcatgt              50
ttacagccat tctatgaaaa agtgttcgga atgtacagac tagcacagaa             100
gctggactaa ttgaacaagt attgctgaaa atgagtgctg tagatgacat             150
gatagcagag taccttcaag tttaaatctg agagtgatat tcatttggca             200
gaacatcata aacaggtttt gtatgatggg aaacttgcaa gtagcattac             250
ctttacatat actgctaagg ccactgatgc tcaactctgc ctggaatcat             300
caccaaaaga gaatgcatca attttttgtgc attcccaaca tgctctaatg            350
cttcagattc aagtgctttt tccactgttt ccccaattgg ataatcggca             400
gctcaatgac agtcaagtgg aaacaactgt ctgctcctgc ttcaggtgca             450
gaaatacagc gatttccagt gccagctgtt gagccagtgc cagcaccagg              500
ggcagattcc cctccaggga cagcgctgga gctagaggaa gctccagagc             550
cctcctgccg ctgccctggg actgcccagg accagcccag tgaggagctg             600
cctgacttca tggcacctcc tgtagagcca ccggcctcag ccctggagct             650
gaaagtgtgg ctggagctag aggtggcaga gaggggtggc cagcacagct             700
ccagccagca gctcccacac tgctcccagt cctgggcaca gtggaagcta             750
tggaggcaga gaccagggtt tgcaatctgg gctcctctgc ctcactggag             800
agggacttct ctcattcagc agagcagcag ccctgctgct gaagggcctg             850
ctgctactgc tgctggggct gtttgcctgc ctgcaggagg tgctggagag             900
caagaaaagg agcctgtgag caggggttcc agcaggtcct cctgctccca             950
gaggcgacct cctcctccag gcatggaggt ttgccctcag ctgggcatct            1000
```

-continued

| | |
|---|---|
| gggccatttg ccccctaacgt gctgcccagg atggcctcct cttgacaggc | 1050 |
| ggacagggggg tgaggggggcc aggggggcatc tccaaaggaa gcttttaaac | 1100 |
| tcagcagctg cacccccagaa tctgtatgcc tgcacctgcc caaggattta | 1150 |
| ttcatagctt acctaagaat ttcaaatttc taccataaca ctgaataaag | 1200 |
| tttgactttt tgaaacttca aa | 1222 |

<210> SEQ ID NO 10
<211> LENGTH: 1513
<212> TYPE: DNA
<213> ORGANISM: Homosapiens
<220> FEATURE:
<223> OTHER INFORMATION: sequence for DKFZP566A1524

<400> SEQUENCE: 10

| | |
|---|---|
| ggggtactcg gcggcggcgg agcgggcggc agagcagggc ggcggcgact | 50 |
| cgcagggtac caccatctta aggacagaaa agctacagga ctctaggagg | 100 |
| ccaccgtcct gatttgggaa gtccaactta ctttggccag acagcagcta | 150 |
| agctggttca tcccatcagc ctggattggt gaaactgaat cacaggagat | 200 |
| atttccaggt ttgctgggat gggaaacctg ctcaaagtcc ttaccaggga | 250 |
| aattgaaaac tatccacact ttttcctgga ttttgaaaat gctcagccta | 300 |
| cagaaggaga gagagaaatc tggaaccaga tcagcgccgt ccttcaggat | 350 |
| tctgagagca tccttgcaga cctgcaggct tacaaaggcg caggcccaga | 400 |
| gatccgagat gcaattcaaa atcccaatga cattcagctt caagaaaaag | 450 |
| cttggaatgc ggtgtgccct cttgttgtga ggctaaagag attttacgag | 500 |
| ttttccatta gactagaaaa agctcttcag agtttattgg aatctctgac | 550 |
| ttgtccaccc tacacaccaa cccaacacct ggaaagggaa caggccctgg | 600 |
| caaaggagtt tgccgaaatt ttacatttta cccttcgatt cgatgagctg | 650 |
| aagatgagga acccggctat tcagaatgac ttcagctact acagaagaac | 700 |
| aatcagtcgc aaccgcatca caacatgca cctagacatt gagaatgaag | 750 |
| tcaataatga gatggccaat cgaatgtccc tcttctatgc agaagccacg | 800 |
| ccaatgctga aaacccttag caatgccaca atgcactttg tctctgaaaa | 850 |
| caaaactctg ccaatagaga acaccacaga ctgcctcagc acaatgacaa | 900 |
| gtgtctgtaa agtcatgctg gaaactccgg agtacagaag taggtttacg | 950 |
| agtgaagaga ccctgatgtt ctgcatgagg gtgatggtgg gagtcatcat | 1000 |
| cctctatgac catgtccacc ctgtgggagc tttctgcaag acatccaaga | 1050 |
| tcgatatgaa aggctgcata aaagttttga aggagcaggc cccagacagt | 1100 |
| gtggagggggc tgctaaatgc cctcaggttc actacaaagc acttgaacga | 1150 |
| tgaatcaact tccaaacaga ttcgagcaat gcttcagtag agctctgctc | 1200 |
| aaagaagagg atctatgtgc tgacctcaga agatgtatat gtttacataa | 1250 |
| tttaatacag attgatgtta atacttgtgt atttacataa ccgtttcctt | 1300 |
| cttgtcactg aaatatatgg acctaatttt gtatcctgac tgactcaacc | 1350 |
| cagcagagca taaattgact tgagagcctt acctttgatg tctgaaatga | 1400 |
| aaccccccttc tccaaaggca aaattcggag actttgatct ttgctactgg | 1450 |
| agtcctttaa caacatctat aacgataaaa aattcctaat tgtcaaaaaa | 1500 | aaaaaaaaaa aaa                                                      1513

<210> SEQ ID NO 11
<211> LENGTH: 1912
<212> TYPE: DNA
<213> ORGANISM: Homosapiens
<220> FEATURE:
<223> OTHER INFORMATION: sequence for LOC51760

<400> SEQUENCE: 11

| | |
|---|---|
| cccaggcgcc ccggccttat tccagcctgg ggagcgcctc ggtggggagc | 50 |
| acgggacagc gagggaggcc gaggcggggg ccctgggcgc ccgatatctc | 100 |
| cgaaccgggg aggcggcccc gattccgaga gccggaacgc agggaaaggc | 150 |
| aaggacgggg cggccggcgg aggggcgggc gccgctcatc agccacgcca | 200 |
| gtcacgtctg gggccaccgg ctgccttttt cttcctttcc ccctttgctt | 250 |
| tcttccccct ccgctgttgg cgagggcaaa gtggccgtgg cggcgccatg | 300 |
| cccgggccgg agtgagtgcg cgcgggcgaa aatggcgtac atccagttgg | 350 |
| aaccattaaa cgagggtttt cttctagaa tctctggtct gctgctgtgc | 400 |
| agatggacct gccggcactg ctgtcagaag tgctacgagt ccagctgttg | 450 |
| ccagtcaagt gaggatgaag ttgaaattct gggacctttc cctgctcaga | 500 |
| cccctccctg gctgatggcc agccggagca gtgacaagga tggtgactct | 550 |
| gtccacacgg ccagcgaagt cccgctgacc ccacggacca attccccgga | 600 |
| tggaagacgc tcgtcctcag acacatccaa gtctacatac agcctgacgc | 650 |
| ggaggatttc gagtcttgag tcaagacgtc ccagctctcc actcatcgat | 700 |
| attaaaccca tcgagtttgg cgttctcagc gccaagaagg agcccatcca | 750 |
| accttcggtg ctcagacgga cctataaccc cgacgctact ttcaggaagt | 800 |
| tcgaacccca cctgtactcc ctcgactcca cagcgacga tgtggactct | 850 |
| ctgacagacg aggagatcct gtccaagtac cagctgggca tgctgcactt | 900 |
| cagcactcag tacgacctgc tgcacaacca cctcaccgtg cgcgtgatcg | 950 |
| aggccaggga cctgccacct cccatctccc acgatggctc cgccaggac | 1000 |
| atggcgcact ccaaccccta cgtcaagatc tgtctcctgc cagaccagaa | 1050 |
| gaactcaaag cagaccgggg tcaaacgcaa gacccagaag cccgtgtttg | 1100 |
| aggagcgcta caccttcgag atccccttcc tggaggccca gaggaggacc | 1150 |
| ctgctcctga ccgtggtgga ttttgataag ttctcccgcc actgtgtcat | 1200 |
| tgggaaagtt tctgtgcctt tgtgtgaagt tgacctggtc aagggcgggc | 1250 |
| actggtggaa ggcgctgatt cccagttctc agaatgaagt ggagctgggg | 1300 |
| gagctgcttc tgtcactgaa ttatctccca agtgctggca gactgaatgt | 1350 |
| tgatgtcatt cgagccaagc aacttcttca gacagatgtg agccaaggtt | 1400 |
| cagaccccctt tgtgaaaatc cagctggtgc atggactcaa acttgtgaaa | 1450 |
| accaagaaga cgtccttctt aaggggcaca attgatcctt tctacaatga | 1500 |
| atccttcagc ttcaaagttc cccaagaaga actggaaaat gccagcctag | 1550 |
| tgtttacagt tttcggccac aacatgaaga gcagcaatga cttcatcggg | 1600 |
| aggatcgtca ttggccagta ctcttcaggc ccctctgaga ccaaccactg | 1650 |

| | |
|---|---|
| gaggcgcatg ctcaacacgc accgcacagc cgtggagcag tggcatagcc | 1700 |
| tgaggtcccg agctgagtgt gaccgcgtgt ctcctgcctc cctggaggtg | 1750 |
| acctgagggc tgcagggaag gcagctttca tttgtttaaa aaaaaaaaaa | 1800 |
| aaagacggaa aaaaatgtgt cacatactat tacatccaca cctgcataca | 1850 |
| cactcgcaac atgtctacac acgtccacac acacagacac acagatacccc | 1900 |
| caaatcctct ca | 1912 |

<210> SEQ ID NO 12
<211> LENGTH: 12747
<212> TYPE: DNA
<213> ORGANISM: Homosapiens
<220> FEATURE:
<223> OTHER INFORMATION: sequence for FLG

<400> SEQUENCE: 12

| | |
|---|---|
| cttttggtga acaaggttca catttattgc caaagatgt ctactctcct | 50 |
| ggaaaacatc tttgccataa ttaatctttt caagcaatat tcaaaaaaag | 100 |
| ataaaaacac tgacacattg agtaaaaaag agctgaagga acttctggaa | 150 |
| aaggaatttc ggcaaatcct gaagaatcca gatgacccag atatggttga | 200 |
| tgtcttcatg gatcacttgg atatagacca caacaagaaa attgacttca | 250 |
| ctgagtttct tctgatggta ttcaagttgg ctcaagcata ttatgagtct | 300 |
| accagaaaag agaatttacc gatatcagga cacaagcaca gaaagcacag | 350 |
| tcatcatgat aaacatgaag ataataaaca ggaagaaaac aaagaaaaca | 400 |
| gaaaaagacc ctcaagtctg aaagaagaa acaatagaaa agggaataag | 450 |
| ggaagatcca agagcccaag agaaacaggg gggaaaaggc atgaatctag | 500 |
| ttctgaaaaa aaagaaagaa aaggatattc acctactcat agagaagaag | 550 |
| aatatggaaa aaaccatcat aactcaagta aaaaagagaa aaacaagact | 600 |
| gaaaatacta gattaggaga caataggaag aggctaagtg aaagacttga | 650 |
| agagaaagaa gacaatgaag aaggagtata tgattatgaa aatacaggaa | 700 |
| gaatgactca aaaatggata caatcaggcc atattgccac atattacaca | 750 |
| atccaggatg aagcctatga caccactgat agtctattag aagaaaacaa | 800 |
| aatatatgaa agatcaaggt catctgatgg caaatcatca tctcaagtga | 850 |
| acaggtcaag acatgaaaat acaagccagg taccattgca ggagtccagg | 900 |
| acaagaaagc gtaggggatc cagagttagc caggacaggg acagtgaggg | 950 |
| acactcagaa gactctgaga ggcactctgg gtcggcttcc agaaaccatc | 1000 |
| atggatctgc gtgggagcag tcaagagatg gctccagaca ccccaggtcc | 1050 |
| catgatgaag acagagccag tcatgggcac tctgcagaca gctccagaca | 1100 |
| atcaggcact cgtcacgcag agacttcctc tcgtggacag actgcatcat | 1150 |
| cccatgaaca ggcaagatca agtccaggag aaagacatgg atccggccac | 1200 |
| cagcagtcag cagacagctc cagacactca gccactgggc gcgggcaagc | 1250 |
| ttcatctgca gtcagcgatc gtggacaccg ggggtctagc ggtagtcagg | 1300 |
| ccagtgacag tgaggacat tcagaaaact cagacacaca atcagtgtca | 1350 |
| ggccacggaa aggctgggct gagacagcag agccaccaag agtccacacg | 1400 |
| tggccggtca ggggaacggt ctggacgttc agggtcttcc ctctaccagg | 1450 |

```
tgagcactca tgaacagcct gactctgccc atggacggac cgggaccagc       1500
actggaggaa gacaaggatc gcaccacgag caggcacgag acagctccag       1550
gcattcagcg tcccaagagg gtcaggacac cattcgtgga cacccggggt       1600
caagcagagg aggaaggcag ggatcccacc acgagcaatc ggtaaatagg       1650
tctggacact caggttccca tcacagccac accacatccc agggaaggtc       1700
tgatgcctcc catgggcagt caggatccag aagtgcaagc agacaaacac       1750
gaaatgagga acaatcagga gacggcacca ggcactcagg gtcacgtcat       1800
catgaagctt cctctcaggc tgacagctct agacactcac aggtgggcca       1850
gggacaatca tcggggccca ggacaagtag gaaccaggga tccagtgtta       1900
gccaggacag tgacagtcag ggacactcag aagactctga gaggtggtct       1950
gggtctgctt ccagaaacca tcatggatct gctcaggagc agtcaagaga       2000
tggctccaga caccccaggt cccatcacga agacagagct ggtcatgggc       2050
actctgcaga cagctccaga aaatcaggca ctcgtcacac acagaattcc       2100
tctagtggac aggctgcgtc atcccatgaa caggcaagat caagtgcagg       2150
agaaagacat ggatcccgcc accagctcca gtcagcagac agctccagac       2200
actcaggcac tgggcacgga caagcttcat ctgcagtcag agacagtgga       2250
caccgagggt ccagtggtag tcaggccact gacagtgagg gacattcaga       2300
agactcagac acacagtcag tgtcaggcca tggacaggct ggtcaccatc       2350
agcagagcca ccaagagtcc gcacgtgacc ggtcagggga aggtctcga       2400 cgttcagggt ctttcctcta ccaggtgagc actcataaac agtctgagtc       2450
ctcccatgga tggacagggc ccagcactgg agtaagacaa ggatcccacc       2500
atgagcaggc acgagacaac tccaggcact cagcatccca agatggtcag       2550
gacaccattc gtggacaccc ggggtcaagc agaagaggaa ggcagggggtc      2600 ccaccacgag caatcggtag ataggtctgg acactcaggg tcccatcaca       2650
gccacaccac atcccaggga aggtctgatg cctcccgtgg gcagtcagga       2700
tccagaagtg caagcagaac aacacgtaat gaggaacaat caagagacgg       2750
ctccaggcac tcagggtcac gtcaccatga agcttcctct catgccgaca       2800
tctctagaca ctcacaggca ggccagggac aatcagaggg gtccaggaca       2850
agcaggcgcc agggatccag tgttagccag gacagtgaca gtgagggaca       2900 ttcagaaagac tctgagaggt ggtctgggtc tgcttccaga aaccatcgtg      2950
gatctgctca ggagcagtca agacatggct ccagacaccc caggtcccat       3000
cacgaagaca gagccggtca cgggcactct gcagacagct ccagacaatc       3050
aggaactcct cacgcagaga cttcctctgg tggacaggct gcgtcatccc       3100
atgaacaggc aagatcaagt ccaggagaaa gacacggatc cgccaccag        3150 cagtcagcag acagctccag acactcaggc attccgcgca gacaagcttc       3200
atctgcagtc agagacagtg gacactgggg gtccagtggt agtcaggcca       3250
gtgatagtga gggacattca gaggagtcag acacacagtc agtgtcaggc       3300
catggacagg atgggcccca tcagcagagc accaagagt ccgcacgtga        3350 ctggtcaggg ggaaggtctg gacgttcagg gtctttcatc taccaggtga       3400
```

```
gcactcatga acagtctgag tctgcccatg ggcggaccag gaccagcact    3450
ggacgaagac aaggatccca ccacgagcag gcacgagaca gctccaggca    3500
ctcagcgtcc caagagggtc aggacaccat tcgtgcacac ccggggtcaa    3550
ggagaggagg aaggcaggga tcccaccatg agcaatcggt agatagatct    3600
ggacactcag ggtccatca cagccacacc acatcccagg gaaggtctga    3650
tgcctcccat gggcagtcag gatccagaag tgcaagcaga caaactcgta    3700
aggacaaaca atcaggagac ggctccaggc actcagggtc acgtcaccat    3750
gaagctgcct cttgggctga cagctctaga cactcacagg tgggacagga    3800
acaatcatcg gggtccagga caagcaggca ccagggatcc agtgttagcc    3850
aggacagtga cagtgagaga cactcagacg actccgagag gttgtctggg    3900
tctgcttcca gaaaccatca tggatcttct cgggagcagt caagagatgg    3950
ctccagacac cctgggttcc atcaagaaga cagagccagt cacgggcact    4000
ctgcagacag ctccagacaa tcaggcactc atcacacaga gtcttcctct    4050
catggacagg ctgtgtcatc ccatgaacag gcaagatcaa gtccaggaga    4100
aagacatgga tcccgccacc agcagtcagc agacagctcc agacactcag    4150
gcattgggca cagacaagct tcatctgcag tcagagacag tggacaccga    4200
gggtccagtg gtagtcaggt cactaacagt gagggacatt cagaagactc    4250
agacacacag tcagtgtcag cccacggaca agctgggccc catcagcaga    4300
gccacaaaga gtccgcacgt ggccagtcag gggaaagctc tggacgttca    4350
aggtctttcc tctaccaggt gagctctcat gaacagtctg agtccacaca    4400
cggacagact gcacccagca ctggaggaag acaaggatcc cgccatgagc    4450
aggcacgaaa cagctctagg cactcagcat cccaagacgg tcaggacacc    4500
attcgtggac acccggggtc aagcagagga ggaaggcagg gatcctacca    4550
cgagcaatca gtagataggt ctggacactc agggtaccat cacagccaca    4600
ccacacccca gggaaggtct gatgcctccc atgggcagtc aggacccaga    4650
agtgcaagca ggcaaacaag aaatgaggaa caatcaggag acggctccag    4700
gcactcaggg tcacgtcacc atgaaccttc cactcgggcc ggcagctcta    4750
gacactcaca ggtgggccag ggagaatcag cggggtccaa gacaagcagg    4800
cgccagggat ccagtgttag tcaggacagg gacagtgagg gacactcaga    4850
agactctgag aggcggtctg agtcggcttc cagaaaccat tatggatctg    4900
ctcgggagca gtcaagacat ggctccagga accccaggtc ccatcaagaa    4950
gatagagcca gtcatgggca ctctgcagag agctccagac aatcaggcac    5000
tcgtcatgca gagacttcct ctggtggaca ggctgcatca tcccaggaac    5050
aggcaaggtc aagtccagga gaaagacatg gatcccgcca ccagcagtca    5100
gcagacagct ccacagactc aggcactggg cgcagacaag attcatctgt    5150
agtcggagac agtggaaacc gagggtccag tggtagccag gccagtgaca    5200
gcgagggaca ctcagaagag tcagacacac agtcagtgtc agcccacgga    5250
caggctgggc cccatcagca gagccaccaa gagtccacac gtggccagtc    5300
agggaaagg tctggacgtt cagggtcttt cctctaccag gtgagcactc    5350
atgaacagtc tgagtccgcc catggacgca cagggcccag cactggagga    5400
```

-continued

```
agacaaagat cccgccacga gcaggcacga gacagctcca ggcactcagc    5450
gtcccaagag ggtcaggaca ccattcgtgg acacccaggg tcaagcagag    5500
gaggaaggca gggatcccac tatgagcaat cggtagatag ttctggacac    5550
tcagggtctc atcacagcca caccacgtcc caggaaaggt ctgatgtctc    5600
ccgtgggcag tcaggatcca gaagtgtcag cagacaaaca cgtaatgaga    5650
aacaatcagg agacggctcc aggcactcag ggtcgcgtca ccatgaagct    5700
tcctctcggg ccgacagctc tagacactcg caggtgggcc agggacaatc    5750
atcagggccc aggacaagca ggaaccaggg atccagtgtt agccaggaca    5800
gtgacagtca gggacactca gaagactctg agaggtggtc tgggtctgct    5850
tccagaaacc atcttggatc tgcttgggag cagtcaagag atggctccag    5900
acaccctggg tcccatcacg aagacagagc cggtcacggg cactctgcag    5950
acagctccag acaatcaggc actcgtcaca cagagtcttc ctctcgtgga    6000
caggctgcgt catcccatga acaggcaaga tcaagtgcag gagaaagaca    6050
tggatcccac caccagctcc agtcagcaga cagctccaga cactcaggca    6100
ttgggcatgg acaagcttca tctgcagtca gagacagtgg acaccgaggg    6150
tacagtggta gtcaggccag tgacagtgag ggacattcag aagactcaga    6200
cacacagtca gtgtcagcac agggaaaagc tgggccccat cagcagagcc    6250
acaaagagtc cgcacgtggc cagtcagggg aaagctctgg acgttcaggg    6300
tctttcctct accaggtgag cactcatgaa cagtctgagt ccacccatgg    6350
acagtctgcg cccagcactg gaggaagaca aggatcccat tatgatcagg    6400
cacaagacag ctccaggcac tcagcatccc aagagggtca ggacaccatt    6450
cgtggacacc cggggccaag cagaggagga agacaggggt cccaccaaga    6500
gcaatcggta gataggtctg acactcaggt ctcatcac agccacacca     6550
catcccaggg aaggtctgat gcctcccgtg ggcagtcagg atccagaagt    6600
gcaagcagaa aaacatatga caaggaacaa tcaggagatg gctctaggca    6650
ctcagggtcg catcatcatg aagcttcctc ttgggccgac agctctagac    6700
actcactggt gggccaggga caatcatcag ggcccaggac aagcaggccc    6750
cggggatcca gtgttagcca ggacagtgac agtgagggac actcagaaga    6800
ttctgagagg cggtctgggt ctgcgtccag aaaccatcat ggatctgctc    6850
aggagcagtc aagagatggc tccagacacc ccaggtccca tcacgaagac    6900
agagccggtc atgggcactc tgcagagagc tccagacaat caggcactca    6950
tcatgcagag aattcctctg gtggacaggc tgcatcatcc catgaacagg    7000
caagatcaag tgcaggagag agacacggat cccaccacca gcagtcagca    7050
gacagctcca gacactcagg cattgggcac ggacaagctt catctgcagt    7100
cagagacagt ggacaccgag ggtccagtgg tagtcaggcc agtgacagtg    7150
agggacattc agaagactca gacacacagt cagtgtcagc ccacggacag    7200
gctgggcccc atcagcagag ccaccaagag tccacacgtg gccggtcagc    7250
aggaaggtct ggacgttcag ggtctttcct ctaccaggtg agcactcatg    7300
aacagtctga gtccgcccat ggacggaccg ggaccagcac tggaggaaga    7350
```

| | |
|---|---|
| caaggatccc accacaagca ggcacgagac agctccaggc actcaacgtc | 7400 |
| ccaagagggt caggacacca ttcatggaca cccggggtca agcagtggag | 7450 |
| gaaggcaggg atcccactac gagcaattgg tagatagatc tggacactca | 7500 |
| gggtctcatc acagccacac cacatcccag ggaaggtctg atgcctccca | 7550 |
| tgggcactca ggatccagaa gtgcaagcag acaaactcgt aacgatgaac | 7600 |
| aatcaggaga cggctccagg cactcagggt cgcgtcacca tgaagcttcc | 7650 |
| tctcgggccg acagctctgg acactcgcag gtgggccagg acaatcaga | 7700 |
| ggggcccagg acaagcagga actggggatc cagttttagc caggacagtg | 7750 |
| acagtcaggg acactcagaa gactctgaga ggtggtctgg gtctgcttcc | 7800 |
| agaaaccatc atggatctgc tcaggagcag ctaagagatg gctccagaca | 7850 |
| ccccaggtcc catcaagaag acagagctgg tcatgggcac tctgcagaca | 7900 |
| gctccagaca atcaggcact cgtcacacac agacttcctc tggtggacag | 7950 |
| gctgcatcat cccatgaaca ggcaagatca agtgcaggag aaagacatgg | 8000 |
| atcccaccac cagcagtcag cagacagctc cagacactca ggcattgggc | 8050 |
| acggacaagc ttcatctgca gtcagagaca gtggacaccg agggtacagt | 8100 |
| ggtagtcagg ccagtgacaa tgagggacat tcagaagact cagacacaca | 8150 |
| gtcagtgtca gcccacggac aggctgggtc ccatcagcag agccaccaag | 8200 |
| agtccgcacg tggccggtca ggggaaacgt ctggacattc aggatctttc | 8250 |
| ctctaccagg tgagcactca tgaacagtct gagtcctccc atggatggac | 8300 |
| ggggcccagc actagaggaa gacaaggatc ccgccatgag caggcacaag | 8350 |
| acagctccag gcactcagca tcccaagacg gtcaggacac cattcgtgga | 8400 |
| cacccgggt caagcagagg aggaaggcag gggtaccacc acgagcattc | 8450 |
| ggtagatagc tctggacact cagggtccca tcacagccac accacatccc | 8500 |
| agggaaggtc tgatgcctcc cgtgggcagt caggatccag aagtgcaagc | 8550 |
| agaacaacac gtaatgagga acaatcagga gacggctcca ggcactcagg | 8600 |
| gtcgcgtcac catgaagctt ccactcatgc cgacatctct agacactcac | 8650 |
| aggcagtcca gggacaatca gagggtccag gagaagcag gcgccaggga | 8700 |
| tccagtgtga gccaggacag tgacagtgag ggacattcag aagactctga | 8750 |
| gaggtggtct gggtctgctt ccagaaacca tcatggatct gctcaggagc | 8800 |
| agctaagaga tggctccaga caccccaggt cccatcaaga agacagagct | 8850 |
| ggtcatgggc actctgcaga cagctccaga caatcaggca ctcgtcacac | 8900 |
| acagacttcc tctggtggac aggctgcatc atcccatgaa caggcaagat | 8950 |
| caagtgcagg agaaagacat ggatcccacc accagcagtc agcagacagc | 9000 |
| tccagacact caggcattgg gcacggacaa gcttcatctg cagtcagaga | 9050 |
| cagtggacac cgagggtaca gtggtagtca ggccagtgac aatgagggac | 9100 |
| attcagaaga ctcagacaca cagtcagtgt cagcccacgg acaggctggg | 9150 |
| tcccatcagc agagccacca agagtccgca cgtggccggt caggggaaac | 9200 |
| gtctggacat tcaggatctt tcctctacca ggtgagcact catgaacagt | 9250 |
| ctgagtcctc ccatggatgg acggggccca gcactagagg aagacaagga | 9300 |
| tcccgccatg agcaggcaca agacagctcc aggcactcag catcccaata | 9350 |

```
cggtcaggac accattcgtg gacacccggg gtcaagcaga ggaggaaggc      9400
aggggtacca ccacgagcat tcggtagata gctctggaca ctcagggtcc      9450
catcacagcc acaccacatc ccagggaagg tctgatgcct cccgtgggca      9500
gtcaggatcc agaagtgcaa gcagaacaac acgtaatgag gaacaatcag      9550
gagacagctc caggcactca gtgtcacgtc accatgaagc ttccactcat      9600
gccgacatct ctagacactc acaggcagtc cagggacaat cagaggggtc      9650
caggagaagc aggcgccagg gatccagtgt gagccaggac agtgacagtg      9700
agggacattc agaagactct gagaggtggt ctgggtctgc ttccagaaac      9750
catcgtggat ctgttcagga gcagtcaagg cacggctcca gacacccag       9800
gtcccatcac gaagacagag ccggtcacgg gcactctgca gaccgctcca      9850
gacaatcagg cactcgtcac gcagagactt cctctggtgg acaggctgca      9900
tcatcccatg aacaggcaag atcaagtcca ggagagagac acggatcccg      9950
ccaccagcag tcagcagaca gctccagaca ctcaggcatt ccgcgtggac     10000
aagcttcatc tgcagtcaga gacagtagac actgggggtc cagtggtagt     10050
caggccagtg atagtgaggg acattcagaa gagtcagaca cacagtcagt     10100
gtcaggccat ggacaggctg ggccccatca gcagagccac caagagtccg     10150
cacgtgaccg gtcaggggga aggtctggac gttcagggtc tttcctctac     10200
caggtgagca ctcatgaaca gtctgagtct gcccatgggc ggaccaggac     10250
cagcactgga cgaagacaag gatcccacca cgagcaggca cgagacagct     10300
ccaggcactc agcgtcccaa gagggtcagg acaccattcg tggacacccg     10350
gggtcaagca gaagaggaag gcagggatcc cactacgagc aatcggtaga     10400
taggtctgga cactcagggt cccatcacag ccacaccaca tcccagggaa     10450
ggtctgatgc ctcccgtggg cagtcaggat ccagaagtgc cagcagacaa     10500
actcgtaatg acgaacaatc aggagatggc tccaggcact catggtcgca     10550
tcaccatgaa gcttccactc aggcggacag ctctagacac tcacagtccg     10600
gccagggaca atcagcgggg cccaggacaa gcaggaacca gggatccagt     10650
gttagccagg acagtgacag tcagggacac tcagaagact ctgagaggtg     10700
gtctgggtct gcttccagaa accatcgtgg atctgctcag gagcagtcaa     10750
gagatggctc cagacacccc acgtcccatc acgaagacag agccggtcac     10800
gggcactctg cagagagctc cagacaatca ggcactcatc atgcagagaa     10850
ttcctctggt ggacaggctg catcatccca tgaacaggca agatcaagtg     10900
caggagagag acatggatcc caccaccagc agtcagcaga cagctccaga     10950
cactcaggca ttgggcacgg acaagcttca tctgcagtca gagacagtgg     11000
acaccgaggt tccagtggta gtcaggccag tgacagtgag ggacattcag     11050
aagactcaga cacacagtca gtgtcagccc acggacaggc tgggccccat     11100
cagcagagcc accaagagtc cacacgtggc cggtcagcag gaaggtctgg     11150
acgttcaggg tctttcctct accaggtgag cactcatgaa cagtctgagt     11200
ctgcccatgg acgggctggg cccagtactg gaggaagaca aggatcccgc     11250
cacgagcagg cacgagacag ctccaggcac tcagcgtccc aagagggtca     11300
```

| | |
|---|---|
| ggacaccatt cgtggacacc cggggtcaag gagaggagga agacagggat | 11350 |
| cctaccacga gcaatcggta gataggtctg gacactcagg gtcccatcac | 11400 |
| agccacacca catcccaggg aaggtctgat gcctcccatg ggcagtcagg | 11450 |
| atccagaagt gcaagcagag aaacacgtaa tgaggaacag tcaggagacg | 11500 |
| gctccaggca ctcagggtcg cgtcaccatg aagcttccac tcaggctgac | 11550 |
| agctctagac actcacagtc cggccagggt gaatcagcgg ggtccaggag | 11600 |
| aagcaggcgc cagggatcca gtgttagcca ggacagtgac agtgaggcat | 11650 |
| acccagagga ctctgagagg cgatctgagt ctgcttccag aaaccatcat | 11700 |
| ggatcttctc gggagcagtc aagagatggc tccagacacc ccggatcctc | 11750 |
| tcaccgcgat acagccagtc atgtacagtc ttcacctgta cagtcagact | 11800 |
| ctagtaccgc taaggaacat ggtcacttta gtagtctttc acaagattct | 11850 |
| gcgtatcact caggaataca gtcacgtggc agtcctcaca gttctagttc | 11900 |
| ttatcattat caatctgagg gcactgaaag gcaaaaaggt caatcaggtt | 11950 |
| tagtttggag acatggcagc tatggtagtg cagattatga ttatggtgaa | 12000 |
| tccgggttta gacactctca gcacggaagt gttagttaca attccaatcc | 12050 |
| tgttgttttc aaggaaagat ctgatatctg taaagcaagt gcgtttggta | 12100 |
| aagatcatcc aaggtattat gcaacgtata ttaataagga cccaggttta | 12150 |
| tgtggccatt ctagtgatat atcgaaacaa ctgggattta gtcagtcaca | 12200 |
| gagatactat tactatgagt aagaaattaa tggcaaagga attaatccaa | 12250 |
| gaatagaaga atgaagcaag ttcactttca atcaagaaac ttcataatac | 12300 |
| tttcagggaa gttatctttt cctgtcaatc tgtttaaaat atgctatagt | 12350 |
| atttcattag tttggtggta gcttattttt attgtgtaat gatctttaaa | 12400 |
| cgctatattt cagaaatatt aaatggaaga aatcaatatc atggagagct | 12450 |
| aactttagaa aactagctgg agtatttag gagattctgg gtcaagtaat | 12500 |
| gttttatgtt tttgaaagtt taagtttag acactcccca aatttctaaa | 12550 |
| ttaatctttt tcagaaatat cgaaggagcc aaaaatataa aacagttctg | 12600 |
| tataccaaag tggctatatc aacatcaggg ctagcacatc tttctctatt | 12650 |
| atccttctat tggaattcta gtattctgta ttcaaaaaat catcttggac | 12700 |
| ataattaata ttatagtaag ctgcatctaa attaaaaata aactatt | 12747 |